US005725854A

United States Patent [19]

Selawry

[11] Patent Number: 5,725,854
[45] Date of Patent: Mar. 10, 1998

[54] METHODS OF TREATING DISEASE USING SERTOLI CELLS AN ALLOGRAFTS OR XENOGRAFTS

[75] Inventor: Helena P. Selawry, Memphis, Tenn.

[73] Assignee: Research Corporation Technologies, Inc., Tucson, Ariz.

[21] Appl. No.: 421,641

[22] Filed: Apr. 13, 1995

Related U.S. Application Data

[63] Continuation-in-part of Ser. No. 211,695, Apr. 13, 1994, abandoned.

[51] Int. Cl.$^6$ .............................. A01N 63/00; C12N 5/00
[52] U.S. Cl. ...................................... 424/93.7; 435/240.1
[58] Field of Search ........................ 424/93.7; 435/240.1

[56] References Cited

FOREIGN PATENT DOCUMENTS 42 27066 A1   8/1992   Germany.

OTHER PUBLICATIONS

Selawry et al., (1988) "Intratesticular Islet Xenograft Survival in Relation to Tissue Cyclosporine Levels", *The American Journal of Medical Science*, 295(6): 497–502.

Whittington et al., (1991) "Islet Allografts in the Cryptorchid Test of Spontaneously Diabetic BB/W or dp Rats: Response to Glucose, Glipizide, and Arginine", *Endo.* 128(6): 2671–2677.

Tze et al., (1990) "Human Islet Xenograft Survival in Diabetics Rats", *Transplantation*, 43(3): 502–505.

Korsgren et al., (1993) "Pancreatic Islet Transplantation in the Human", *Advances in Nephrology*, 22: 371–387.

Barker et al., (1991) "Studies of Privileged Sites and Islet Transplantation", *Transplantation Proceedings*, 23:(4) 2138–2142.

Cameron et al., (1990) "Successful Islet Abdominal Testis Transplantation Does Not Require Leydig Cell", *Transplantation*, 50:(4) 649–653.

Groth et al., (1994) "Transplantation of Porcine Fetal Pancreas to Diabetic Patients", *Lancet*, 344: 1402–04.

Selawry et al., (1994) "Extended Functional Survival of Abdominal Intratesticular Islet Alografts in Rhesus-Monkeys", *Diabetes*, 43: PA162.

Selawry et al., (1989) "Abdominal Intratesticular Islet-Xenograft Survival in Rats", *Diabetes*, 38:(1) 220–223.

Soon-Shiong et al., (1993) "Long-Term Reversal of Diabetes by the Injection of Immunoprotected Islets",*Proc. Nat'l Acad. Sci. USA*, 90: 5843–5847.

Soon-Shiong et al., (1994) "Insulin Independence in a Type 1 Diabetic Patient After Encapsulated Islet Transplantation", *Lancet*, 343: 950–951.

Tze, et al., (1992) "Transplantation of Discordant Pig Islet Xenografts in Diabetic Rats", *Diabetes Research and Clinical Practice*, 15: 197–204.

Tze et al., (1993) "Diabetic Rabbit Model For Pig Islet Xenotransplantation", *Transplantation*, 56:(6) 1348–1352.

Tze et al., (1994) "Prolongation of Pig Islet Xenograft in Rats By Local Immunosuppression with FK 506", *Transplantation Proceedings*, 26:(2) 777–778.

Selawry et al., (1993) "Sertoli Cell-Enriched Fractions in Successful Islet Cell Transplantation", *Cell Transplantation*, 2: 123–129.

Dahaney, D.G., (Jul., 1991), "A biochemical and immunohistochemical study of rat Sertoli cells", *Chemical Abstracts* 115(3): 26534–26535.

Hutson et al. (Mar., 1993), "Sertoli cell function in diabetic, insulin–treated diabetic, and semi–starved rats", *Chemical Abstracts* 98(13): 105350–105351.

Selawry, et al. (Nov. 1991) "Production of a Factor, or Factors, Suppressing IL–2 Production and T Cell Proliferation by Sertoli Cell–Enriched Preparations. A Potential Role for Islet Transplantation in an Immunologically Privileged Site", *Transplantation* 52(5): 846–850.

Oonk, et al. (1988) "Insulin–Like Growth Factor I (IGF–I) Receptors on Steroli Cells from Immature Rats and Age–Dependent Testicular Binding of IGF–I and Insulin", *Molecular and Cellular Endocrinology* 55:33–43.

Whitmore III, et al. (Oct. 1985) "The Role of Germinal Epithelium and Spermatogenesis in the Privileged Survival Intratesticular Grafts", *The Journal of Urology* 134(4): 782–786.

Hofmann, et al. (Aug. 1992), Abstract No. 92347475 "Immortalization of Germ Cells and Somatic Testicular Cells Using the SV40 Large T Antigen", *Experimental Cell Research* 201(2): 417–435.

Lejeune, et al. (1993), Abstract No. 93:280614 "Enhancement of Testosterone Secretion by Normal Adult Human Leydig Cells b Co–Culture with Enriched Preparations of Normal Adult Human Sertoli Cells", *Int. J. Androl.* 16(1): 27–34.

Berends, et al. (1991), Abstract No. 92:167853 "Significant Improvement of the Survival of Seminoma Cells in vitro by use of a Rat Sertoli Cell Feeder Layer and Serum–Free Medium", *J. Natl. Cancer Inst.* 83(19):1400–1403.

*Primary Examiner*—Michael G. Wityshyn
*Assistant Examiner*—Deborah Ware
*Attorney, Agent, or Firm*—Scully, Scott, Murphy & Presser

[57] ABSTRACT

The present invention describes a method of treating a disease that results from a deficiency of a biological factor which includes administering to a mammal Sertoli cells and cells that produce the biological factor. In particular, the present invention describes a method of treating diabetes mellitus by transplanting pancreatic islet of Langerhans cells in conjunction with Sertoli cells to create an immunologically privileged site. A method of creating an immunologically privileged site in a mammal for cellular transplants is further described by the present invention. A pharmaceutical composition comprising Sertoli cells and cells that produce a biological factor is also provided.

40 Claims, 12 Drawing Sheets

METHODS OF TREATING DISEASE USING SERTOLI CELLS AN ALLOGRAFTS OR XENOGRAFTS

This is a continuation-in-part application of U.S. Ser. No. 08/211,695, filed Apr. 13, 1994, now abandoned.

This invention was made with United States government support under grant DK42421 awarded by the National Institutes of Health. The United States Government may have certain rights in the invention.

FIELD OF THE INVENTION

Transplants of healthy organs or cells into a patient suffering from a disease are often rejected by the body due to an immune response initiated in response to the foreign tissue or cells. The present invention provides a method of cellular transplantation in which an immunologically privileged site is created, thus alleviating the rejection associated with conventional transplantation therapy. Specifically, the present invention describes a method of treating a disease that results from a deficiency of a biological factor which comprises administering to a mammal Sertoli cells and cells that produce the biological factor. In particular, the present invention describes a method of treating diabetes mellitus by transplanting pancreatic islet of Langerhans cells in conjunction with Sertoli cells to create an immunologically privileged site. A method of creating an immunologically privileged site in a mammal for cellular transplants is further described by the present invention. A pharmaceutical composition comprising Sertoli cells and cells that produce a biological factor is also provided.

BACKGROUND OF THE INVENTION

Certain chronic diseases destroy the functional cells in affected organs. Mammals with such diseases are often unable to produce proteins or hormones necessary to maintain homeostasis and usually require numerous exogenous substances to survive. Transplanting healthy organs or cells into a mammal suffering from such a disease may be necessary to save the mammal's life. This type of therapy is generally regarded as a last alternative to curing an otherwise fatal condition. Such transplants, however, are often rejected by the body due to an immune response initiated in response to the foreign tissue or cells. Presently, the only recourse to combat this immune response is to administer chronic nonspecific immunosuppression agents. Unfortunately, this only trades the complications of one chronic disease with other complications caused by the immunosuppression agent.

One disease which scientists have attempted to treat with organ and/or cellular transplants but have had very limited success is diabetes mellitus. Diabetes mellitus is a prevalent degenerative disease in mammals. It is characterized by a relative or complete lack of insulin secretion by the beta cells within the islets of Langerhans of the pancreas or by defective insulin receptors.

This insulin deficiency prevents normal regulation of blood glucose levels and often leads to hyperglycemia and ketoacidosis. When administered to a mammal, insulin promotes glucose utilization, protein synthesis, formation and storage of neutral lipids and the growth of certain cell types.

In the United States alone there are approximately 13 million diabetics. Of these, 2.6 million are insulin dependent diabetics. *Drug & Market Dev.*, 4:210 (1994). Healthcare analysts estimate that diabetes costs $92 billion a year resulting from medical costs and lost productivity.

The various forms of diabetes have been organized into a series of categories developed by the National Diabetes Data Group of the National Institutes of Health. Type I diabetes in this classification scheme includes patients dependent upon insulin to prevent ketosis. This group of diabetics was previously called juvenile-onset diabetes, brittle diabetes or ketosis-prone diabetes. Type I diabetes is caused by an autoimmune reaction that causes complete destruction of beta cells.

Type II diabetes is classified as adult-onset diabetics. The diabetic patient may or may not be insulin dependant. Type II diabetes can be caused by a number of factors. For most mammals with Type II diabetes, the beta islet cells are defective in the secretion of insulin.

There are many therapies currently used to treat diabetes, however, each has its limitations. The major problem confronting most patients with diabetes mellitus is that currently available therapies fail to prevent the complications of the disease process. The most common method of treating Type I diabetes in mammals is providing an endogenous source of insulin such as porcine, bovine or human insulin. Insulin injection therapy prevents severe hyperglycemia and ketoacidosis, but does not completely normalize blood glucose levels. This treatment further fails to prevent the complications of the disease process, including premature vascular deterioration. Premature vascular deterioration is the leading cause of morbidity among diabetic patients. Furthermore, complications resulting from long-term diabetes include renal failure, retinal deterioration, angina pectoris, arteriosclerosis, myocardial infarction and peripheral neuropathy.

A second method of treating diabetes is by transplanting the pancreas in conjunction with the administration of chronic nonspecific immunosuppression agents. This treatment is usually given to an individual who has advanced diabetes, such as an individual with kidney failure. Whole pancreas transplantation can be successfully done with a 75% one-year survival rate, but surgical transplantation of the pancreas is very difficult. Furthermore, since the entire organ must be donated, the only practicable source is a deceased donor. In addition, when cyclosporine, the most common immunosuppressive drug used for organ transplants, is administered in a dosage necessary to suppress the immune response, the drug inhibits pancreatic cell function. Furthermore, the steroids that are often administered with an organ transplant often cause the patient to become diabetic.

A third treatment involves transplanting islet of Langerhans cells into the diabetic patient. However, islet transplantation ha been generally unsuccessful due to the aggressive immune rejection of islet grafts. (Gray. 1991. *Immunology Letters* 29:153; Jung et al.. 1990. *Seminars in Surgical Oncology* 122). In particular, successful transplantation of isolated pancreatic islet cells has been very difficult to achieve due to the chronic administration of immunosuppressive drugs required to prevent organ rejection of the cells following transplantation. These dosages of immunosuppressive drugs can cause increased susceptibility to infection, hypertension, renal failure and tumor growth. Furthermore, unlike most organ transplants, islet cells must grow their own blood supply following implantation in the host in order for the cells to survive. Conventional transplantation techniques do not provide the necessary factors to stimulate the production of new blood vessels.

The present invention alleviates many of the problems associated with the current therapies for chronic diseases that destroy the functional cells of vital organs. In particular, the present invention solves the problems associated with the conventional therapies for diabetes mellitus, by providing a method of transplanting pancreatic islets cells into a diabetic mammal, whereby the cellular transplants produce insulin in the diabetic mammal. The present inventor has previously demonstrated extended functional survival of islet cells allografts and xenografts in the testis. (Selawry et al., 1989. *Diabetes* 38:220.) It has been surprisingly discovered in accordance with the present invention that an immunologically privileged site can be created in a mammal by transplanting Sertoli cells to a nontesticular site in a mammal. The newly created immunologically privileged site allows the transplantation and survival of cells that produce biological factors useful in the treatment of diseases, especially diabetes.

SUMMARY OF THE INVENTION

The present invention relates to a method of treating a disease that results from a deficiency of a biological factor in a mammal which comprises administering Sertoli cells and cells that produce the biological factor. In a preferred embodiment, the biological factor is a hormone.

In a more preferred embodiment, the disease is diabetes mellitus, the factor producing cells are pancreatic islet cells and the factor is insulin.

In yet another embodiment the cells that produce the biological factors are cells that have been genetically engineered, for example by transformation with a nucleic acid that expresses the biological factor.

The present invention further relates to a method of treating diabetes mellitus in a mammal comprising administering pancreatic islet cells and Sertoli cells. In a preferred embodiment the Sertoli cells and islet cells are administered by transplantation.

Another aspect of this invention is directed to a method of creating an immunologically privileged site in a mammal.

Yet another embodiment of the present invention provides a pharmaceutical composition comprising Sertoli cells and cells that produce a biological factor. In a preferred embodiment the pharmaceutical composition comprises Sertoli cells and pancreatic islet cells and a pharmaceutically acceptable carrier.

The present invention further provides a compartmentalized kit containing Sertoli cells and cells that produce a biological factor. An article of manufacture comprising a packaging material and Sertoli cells contained within the packaging is also provided.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 5a shows the plasma glucose (mg/dl) concentrations in response to the oral glucose administration of 2 g/kg of a 50% glucose solution in three groups of rats: untreated control Sprague Dawley, transplanted diabetic BB/Wor dp, and insulin treated diabetic BB/Wor dp rats. FIG. 5b shows the serum insulin levels in response to the same dose of oral glucose in untreated control Sprague Dawley, and in transplanted BB/Wor dp rats.

FIG. 6a shows the plasma glucagon responses to the oral administration of 2 g/kg of a 50% glucose solution in three groups of rats: untreated control Sprague Dawley, transplanted diabetic BB/Wor dp, and insulin treated diabetic BB/Wor dp rats. FIG. 6b shows the plasma glucagon responses to the oral administration of 7 mg/kg of glipizide and 2 g/kg of a 50% glucose solution, administered 30 minutes later, in three groups of rats: untreated control Sprague Dawley, transplanted diabetic BB/Wor dp, and insulin treated diabetic BB/Wor dp rats. Data points are mean±SE of eight animals in each group.

DETAILED DESCRIPTION OF THE INVENTION

Figure 1:
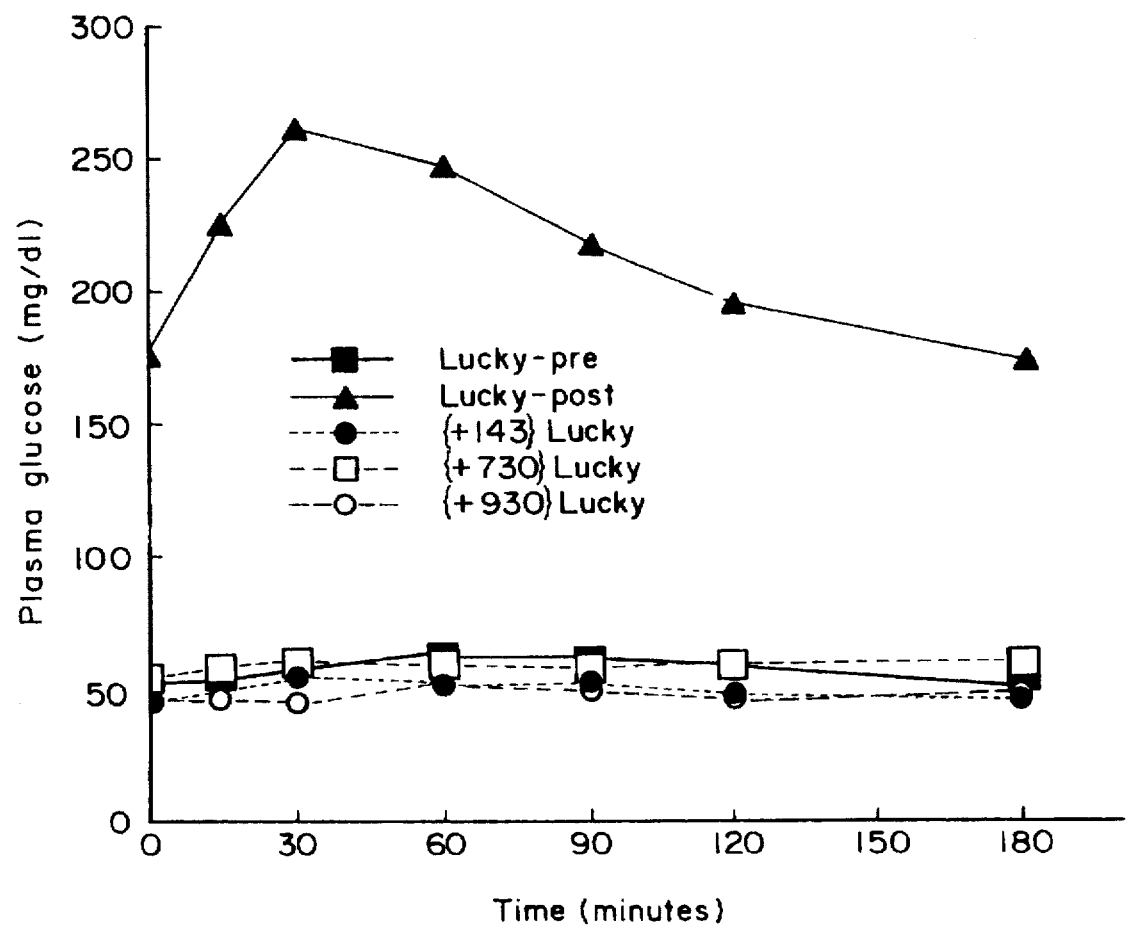
FIG. 1 shows the glucose responses to oral sustacal tolerance tests done on the monkey "Lucky" at intervals before pancreatectomy (Lucky-pre); after pancreatectomy but prior to transplantations (Lucky-post); and at intervals following transplantation (143 days, 730 days and 930 days, respectively).

The present invention is directed to a method of treating a disease that results from a deficiency of a biological factor in mammals which comprises administering to a mammal Sertoli cells and cells that produce the biological factor. As defined by the present invention, a biological factor is a protein or nonprotein compound that is necessary for cellular metabolism and homeostasis. In a preferred embodiment, the biological factor is a hormone. Hormone producing cells which can be administered using the method described in the present invention include, for example, pancreatic islet of Langerhans, pituitary, liver, parathyroid and thyroid cells.

In accordance with the present invention, the Sertoli cells and the cells that produce the biological factor can be from the same species as the mammal to be treated or from a different species. Further, the Sertoli cells and the cells that produce the biological factor need not be derived from the same species. It has been demonstrated in accordance with the present invention that Sertoli cells from pigs in conjunction with islet of Langerhans from pigs can be used in the treatment of diabetes mellitus in rats. In a preferred embodiment the Sertoli cells are bovine, porcine or human.

Sertoli cells, which are the predominant cells of male testes, used in the method described by the present invention can be separated from other testicular cells such as Leydig cells, peritubular cells and germ cells, using conventional techniques. For example, the testes of a male mammal, such as a boar or ram, are first collected by castration. The testes are then chopped into several pieces and subsequently washed by centrifugation.

Testicular Leydig cells can be removed from the tissue suspension using digestion agents such as trypsin and DNase. The remaining cell suspension is then washed by centrifugation several times. The pellet is resuspended in collagenase, incubated and washed by centrifugation to eliminate peritubular cells within the testes. Testicular germ cells can be removed by incubating the pellet with hyaluronidase and DNase. After several washings by centrifugation, the Sertoli cells can be collected to transplant using the method of the present invention.

In accordance with the present invention, a biological factor is a protein or nonprotein compound that is absent, deficient or altered in a disease state. Cells that produce a biological factor can be isolated, for example, by first surgically removing the tissue that produces the factor from a mammal. This tissue is subsequently chopped and digested using conventional techniques. For example, the tissue can be digested using a collagenase digestion. The particular factor producing cells can subsequently be collected from the digestion mixture using a separation gradient such as a Ficoll gradient. The factor producing cells are then grown in tissue culture in serum using conventional techniques. The factor producing cells may be co-cultured with Sertoli cells in tissue culture. Cells grown in tissue culture can be transplanted into a mammal in conjunction with the Sertoli cells using the method of the present invention. In accordance with the present invention, factor producing cells may be stored using a variety of conventional techniques, such as cryopreserving the cells prior to growth in tissue culture for subsequent transplantation. It has been observed in accordance with the present invention, that Sertoli cells co-cultured with factor producing cells such as islet cells enhance the proliferation and recovery rate of the factor producing cells in tissue culture and in particular, enhance the recovery rate and proliferation of factor producing cells that have been previously stored using techniques such as cryopreservation.

In a preferred embodiment the factor is a hormone, and the hormone producing cells are isolated from a tissue source as described above. For example, insulin-producing cells are isolated from the pancreas. In another preferred embodiment, the factor producing cells are provided by transforming suitable host cells with a nucleic acid capable of expressing the factor of interest. Transformed cells are provided by methods known to one of ordinary skill in the art, and can be found in a myriad of textbooks and laboratory mammals, including Sambrook et al. (1989) Molecular Cloning: A Laboratory Mammal, Cold Spring Harbor Laboratories, Cold Spring, New York. If necessary, the nucleic acid encoding the factor of interest can be adapted by methods known to one of ordinary skill in the art to effect secretion of the factor from the transformed cell. The utilization of Sertoli cells in conjunction with the factor producing cells in accordance with the method of the present invention allows the production of an immunologically privileged site in the treated mammal.

The administration of factor producing cells and Sertoli cells into a mammal is accomplished by conventional techniques. In a preferred embodiment, administration is by transplantation and the factor producing cells are injected into the mammal concurrently with or immediately after the injection of the Sertoli cells into the same site. In accordance with the present invention, an exogenous biological factor may be administered following the transplantation of factor producing cells and Sertoli cells until the transplanted cells produce a therapeutically effective amount of the biological factor. For the treatment of diabetes, for example, insulin may be administered following the transplantation of pancreatic islet cells and Sertoli cells until the transplanted islet cells produce a therapeutically effective amount of insulin.

The Sertoli cells and factor producing cells of the present invention can be transplanted using any technique capable of introducing the cells into the mammal such as parenteral administration or subcutaneous administration following surgical exposure to a desired site. Prior to transplantation, the recipient mammal is anesthetized using local or general anesthesia according to conventional technique. In a preferred embodiment the mammal to be treated is human. In another embodiment the present method of treating disease further comprises administering an immunosuppressive agent such as, for example, cyclosporine, tacrolimus, despergualin and monoclonal antibodies to, e.g., T cells. In a preferred embodiment the immunosuppressive agent is cyclosporine. In another preferred embodiment cyclosporine is administered at a dosage of from 0.5 mg to 200 mg/kg body weight. In a most preferred embodiment cyclosporine is administered at a dosage of from 5 mg to 40 mg/kg body weight.

It has been discovered in accordance with the present invention that administration of Sertoli cells and factor producing cells results in the creation of an immunologically privileged site in the treated mammal. An immunologically privileged site as defined by the present invention is a site in the mammal where the immune response produced in response to the transplanted cells is suppressed due to immuno-suppressive agents produced by Sertoli cells. Immunologically privileged sites are characterized by an available blood supply to provide nourishment for the transplanted cells and a dense tissue to keep the transplanted cells within close proximity of each other. Examples of immunologically privileged sites as defined by the present invention include the renal subcapsular space, subcutaneous facie, the brain and the hepatic portal vein.

In accordance with the present invention it has been shown that Sertoli cells increase the rate at which the transplanted factor producing cells vascularize in the transplanted site. It is therefore indicated that the Sertoli cells (i.e. the relevant agents produced by the Sertoli cells) promote the increased vascularization rate of the transplanted cells, for example, islet cells).

In a preferred embodiment, the present invention describes a method of treating diabetes mellitus by transplanting islet of Langerhans in conjunction with Sertoli cells to create an immunologically privileged site. Allografts as used in the present invention describes the transfer of tissues or cells between two genetically dissimilar mammals of the same species. The term xenografts in the present invention describes the transfer of tissues or cells between two mammals of different species.

The transplanted islet of Langerhans cells and Sertoli cells used in the method described by the present invention can be prepared using any number of conventional techniques. For example, islet of Langerhans cells can be prepared from the pancreas of several mammals of the same species. The pancreases are pooled together, chopped up and digested using collagenase. The islet of Langerhans cells can be further isolated using conventional gradients. Once isolated, the islet cells can be grown in culture and then transplanted in conjunction with Sertoli cells to create an immunoprivileged site.

Sertoli cells used in the method described by the present invention can be isolated from mammalian male testes. To collect the islet cells, the testes are first chopped into several pieces and then washed by centrifugation. Leydig cells, present in the crude mixture, can be removed from the tissue suspension using digestion agents such as trypsin and DNase. The remaining cell suspension is then washed by centrifugation several times. Following, the pellet may be resuspended in collagenase, incubated and washed by centrifugation to eliminate peritubular cells within the testes. Testicular germ cells can be removed by incubating the pellet with hyaluronidase and DNase. After several washings by centrifugation, the Sertoli cells for transplantation can be collected.

The Sertoli cells can be transplanted to create an immunoprivileged site within a mammal using a variety of techniques. For example, after the mammal is anesthetized, the Sertoli cells can be injected into a tissue mass, thereby creating an immunoprivileged site.

Sertoli cells are administered in an amount effective to provide an immunologically privileged site. Such an effective amount is defined as that which prevents immune rejection of the subsequently or co-administered cells that produce the biological factor. Immune rejection can be determined for example histologically, or by functional assessment of the factor produced by the cells.

In a preferred embodiment Sertoli cells are administered in amounts ranging from $10^1$ to $10^{10}$ cells. In a more preferred embodiment, $10^5$ to $10^{10}$ cells are administered.

The cells producing the biological factor are administered in a therapeutically effective amount. The ordinary skilled artisan can determine the appropriate amount of cells producing the biological factor by methods known in the art. The amount of cells is dependent upon the amount of factor being produced by the cells and the known therapeutically effective amount of the factor necessary to treat the disease. For example, 1 to 1000 islet cells per gram body weight can be administered to treat diabetes using allografts, 20 to 1000 islets per gram body weight are administered using xenografts. In another preferred embodiment, 5 to 100 islet cells per gram body weight are administered to treat diabetes. In a most preferred embodiment, 5 to 20 islet cells per gram body weight are administered, using allografts and 100–1000 islet cells per gram body weight are administered for xenografts.

In another embodiment the present method of treating diabetes further comprises administering an immunosuppressive agent such as, for example, cyclosporine, tacrolimus, despergualin and monoclonal antibodies to, e.g., T cells. In a preferred embodiment the immunosuppressive agent is cyclosporine. In another preferred embodiment cyclosporine is administered at a dosage of from 0.5 mg to 200 mg/kg body weight. In a most preferred embodiment cyclosporine is administered at a dosage of from 5 mg to 40 mg/kg body weight.

More generally, the immunosuppressive agent can be administered for a time sufficient to permit the transplanted islets to be functional. This period extends from the point prior to or immediately following the transplantation of the islets to the point at which the cells are capable of producing therapeutically effective amounts of insulin. In a preferred embodiment, the sufficient period of time to administer an immunosuppressive agent is about 40 to about 100 days following transplantation of the islets. In a more preferred embodiment, the sufficient period of time is about 50–60 days.

A preferred embodiment of this invention is directed to a method of treating Type I and Type II diabetes mellitus by transplanting islet of Langerhans in conjunction with Sertoli cells into the renal subcapsular space.

Unlike the therapies for diabetes described in the prior art, the method of treating diabetes described by the present invention prevents the complications of the disease process and does not result in the adverse side effects associated with conventional diabetes therapy. Furthermore, the method of transplanting islet cells described by the present invention provides the necessary factors for angiogenesis of the islet transplants.

A method of creating an immunologically privileged site in a mammal is further described by the present invention. An immunologically privileged site is created by transplanting isolated Sertoli cells into a mammal in an amount effective to create an immunologically privileged site. In a preferred embodiment, $10^1$ to $10^{10}$ cells are administered. In a more preferred embodiment, $10^5$ to $10^{10}$ cells are administered. In a preferred embodiment the Sertoli cells are transplanted into the renal subcapsular space or subcutaneous facie by injection. In a preferred embodiment the mammal is a human and the Sertoli cells are human or porcine.

Further contemplated in accordance with the present invention is a method of enhancing the recovery and proliferation of ex vivo cells comprising co-culturing said cells with Sertoli cells for a time and under conditions sufficient to achieve said enhanced recovery and proliferation.

Another aspect of the present invention provides a pharmaceutical composition comprising Sertoli cells and cells producing a biological factor and a pharmaceutically acceptable carrier. In a preferred embodiment the composition comprises Sertoli cells and islet of Langerhans cells and a pharmaceutically acceptable carrier. A further preferred embodiment of the present invention comprises using porcine, bovine or human Sertoli cells and porcine, bovine or human islet of Langerhans cells. As used herein, a pharmaceutically acceptable carrier includes any and all solvents, dispersion media, coatings, antibacterial and antifungal agents, isotonic agents and the like. The use of such media and agents is well-known in the art. The present invention further contemplates a pharmaceutical composition comprising Sertoli cells and a pharmaceutically acceptable carrier.

The present invention is also directed to a kit for treatment of a disease. In one embodiment, the kit is compartmentalized to receive a first container adapted to contain Sertoli cells in an amount effective to create an immunologically privileged site in a mammal, and a second container adapted to contain a therapeutically effective amount of cells that produce a biological factor that is absent or defective in the disease to be treated. In a preferred embodiment, the Sertoli cells are bovine, porcine or human and are provided in an amount of from $10^1$ to $10^{10}$ cells. In a more preferred embodiment, Sertoli cells are provided in an amount of from $10^5$ to $10^{10}$ cells. In another preferred embodiment the cells that produce a biological factor are cells that have been transformed with DNA encoding the factor. In yet another preferred embodiment the cells that produce the factor are pancreatic islet cells. The islet cells are provided in a preferred amount of 5 to 200 cells per gram of body weight, and in a more preferred amount of 5 to 100 cells per gram of body weight.

The present invention further provides an article of manufacture comprising a packaging material and Sertoli cells contained within said packaging material, wherein said Sertoli cells are effective for creating an immunologically privileged site in a mammal, and wherein said packaging material contains a label that indicates that said Sertoli cells can be used for creating an immunologically privileged site in a mammal. The packaging material used to contain the Sertoli cells can comprise glass, plastic, metal or any other suitably inert material.

In order to further illustrate the present invention, the experiments described in the following examples were carried out. It should be understood that the invention is not limited to the specific examples or the details described therein. The results obtained from the experiments described in the examples are shown in the accompanying figures and tables.

EXAMPLE 1

Six male Rhesus monkeys were transplanted with islet allografts in their testes to examine the survival of these transplants. The recipients were made diabetic by means of a near total pancreatectomy, followed two weeks later by an intravenous injection of 35 mg streptozotocin/kg body weight. This procedure resulted in the induction of severe diabetes melitis. Plasma glucose levels were in excess of 400 mg/dl and the animals were ketotic. Malabsorption was prevented by the oral administration of VIOKASE®, one tablet given twice daily before each meal.

Islets were isolated from female Rhesus monkeys. First, the pancreases of five animals were removed, pooled and chopped finely into smaller fragments. After collagenase digestion in a water bath at 37° C., the islets were separated from exocrine tissues and other cellular debris on at least two Ficoll gradients, prepared in tandem. The islets were washed three times by centrifugation in ice-cold Hanks's buffer and then handpicked and transferred in groups of 150 to biologic grade Petri dishes. Each dish contained 6 mL of culture medium CMRL-1066 supplemented with 5% fetal calf serum, glucose at a concentration of 250 mg/dL, penicillin (100 U/mL), and streptomycin (100 µg/mL). Incubation of islets were carried out at 35° C. in 5% $CO_2$ and air for 4 to 6 days. The islets were transferred to fresh medium at 48 hour intervals.

Viability and counting of the islets were facilitated by means of the uptake of the dye dithizone. Each monkey received an average of about $10^4$ islets/kg body weight injected into both testes. In the first three animals the testes were elevated into the abdominal cavity, whereas in the last three recipients the grafted organs were anchored into the inguinal canal. Cyclosporine (CsA) was administered, in varying doses to the first three grafted animals over a 30 day period, whereas the last three hosts were given 7 injections of CsA (20 mg/kg) on days −4 to +3. Oral sustacal tolerance tests were done on day 30, and then at intervals in the normoglycemic animals, as follows.

The monkeys were housed individually in cages and given standard monkey chow and fruit twice daily. In addition, a pancreatic enzyme was mixed with the food since the monkeys had been pancreatectomized to make them diabetic before transplantation.

The night before the test, the animals were fasted for 12 hours. At 8 a.m. the next morning they were then anesthetized and prepared for the test meal. Sustacal was used as the test agent. Sustacal consists of a physiologic mixture of carbohydrates, proteins and fat which closely mimics a standard meal and which is a powerful stimulus for the release of insulin.

Sustacal was injected directly into the stomach of the sleeping animal through a nasogastric tube. Blood samples were then obtained at times 0, 15, 30, 60, 90, 120 and 180 minutes. The samples were centrifuged and the serum stored at −20° C. until measurements for insulin or C-peptide could be carried out. C-peptide is a very sensitive marker for beta cell function. The results are shown in FIGS. 1–4.

FIG. 1 shows the glucose responses to oral sustacal tolerance tests done on the monkey "Lucky" at intervals before pancreatectomy (Lucky-pre); after pancreatectomy but prior to transplantation (Lucky-post); and at intervals following transplantation (143 days, 730 days and 930 days, respectively).

It can be readily appreciated that the animal became severely diabetic after the removal of his pancreas (Lucky-post). Following transplantation the glucose responses were restored to normal levels at all of the time intervals measured (143, 730 and 930 days following transplantation). Lucky showed no evidence of graft failure. With graft failure glucose levels would become elevated would approach those which were found following his pancreatectomy.

Figure 2:
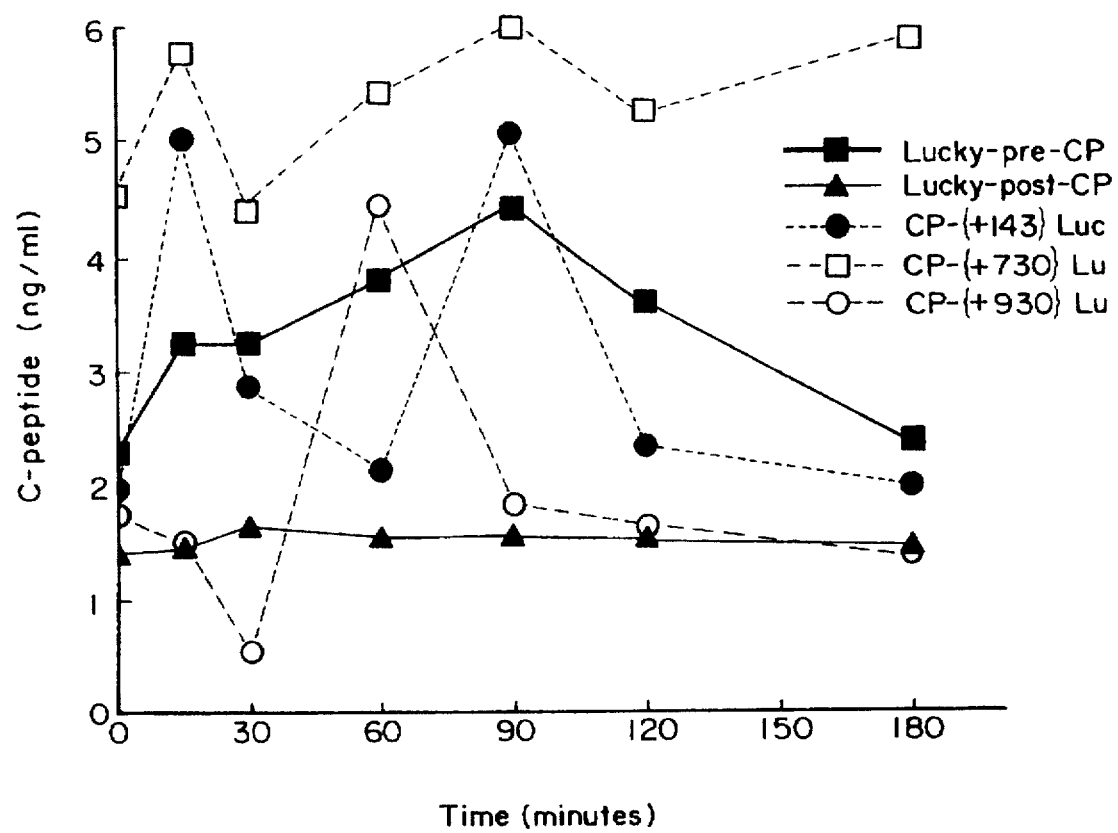
FIG. 2 shows the C-peptide responses to an oral sustacal tolerance test at the same time intervals as depicted in FIG. 1.

FIG. 2 shows the C-peptide responses to an oral sustacal tolerance test at the same time intervals as depicted in FIG. 1. Following his pancreatectomy the C-peptide responses became blunted indicating a severe diabetes. But following transplantation the levels were not only restored to normal but appeared to show a "hyperresponsive" pattern of C-peptide release and levels done on day 730 exceed the normal levels at all points measured. The elevated levels might be due to the fact that insulin released from the testis enters the systemic circulation. By contrast, insulin released from the pancreas enters the portal vein and travels immediately to the liver where about 60% is broken down during the first passage. Insulin released into the systemic circulation reaches the liver much later, thus the elevated levels. As was evident with an investigation of the glucose concentrations, the C-peptide responses showed no evidence of failure 30 months following transplantation.

Figure 3:
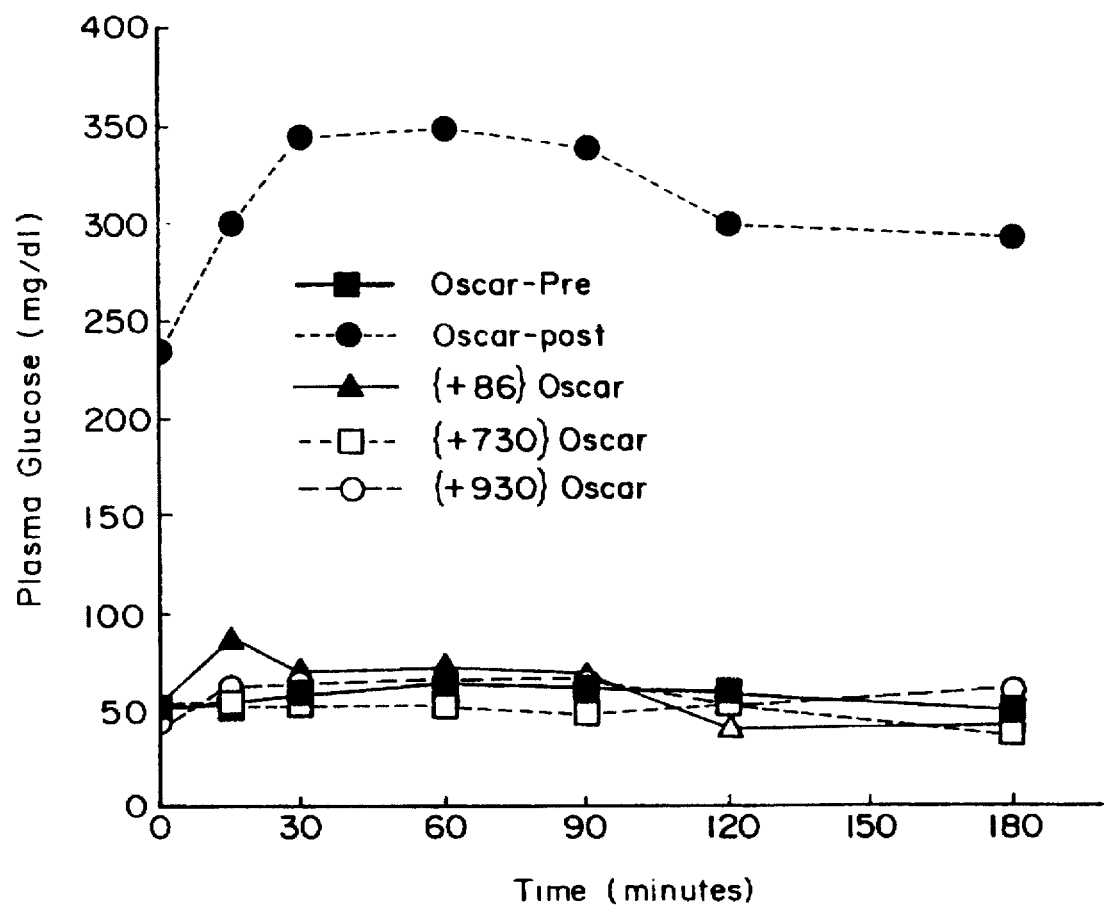
FIG. 3 shows the glucose responses to oral sustacal tolerance tests in the monkey "Oscar"

FIG. 3 shows the glucose responses to oral sustacal tolerance tests in the monkey "Oscar". Following the removal of his pancreas he became severely diabetic with elevated glucose levels. Following transplantation of islets the glucose responses became similar to those determined before his pancreas was removed. The glucose levels remain within normal levels 32 months following transplantation.

Figure 4:
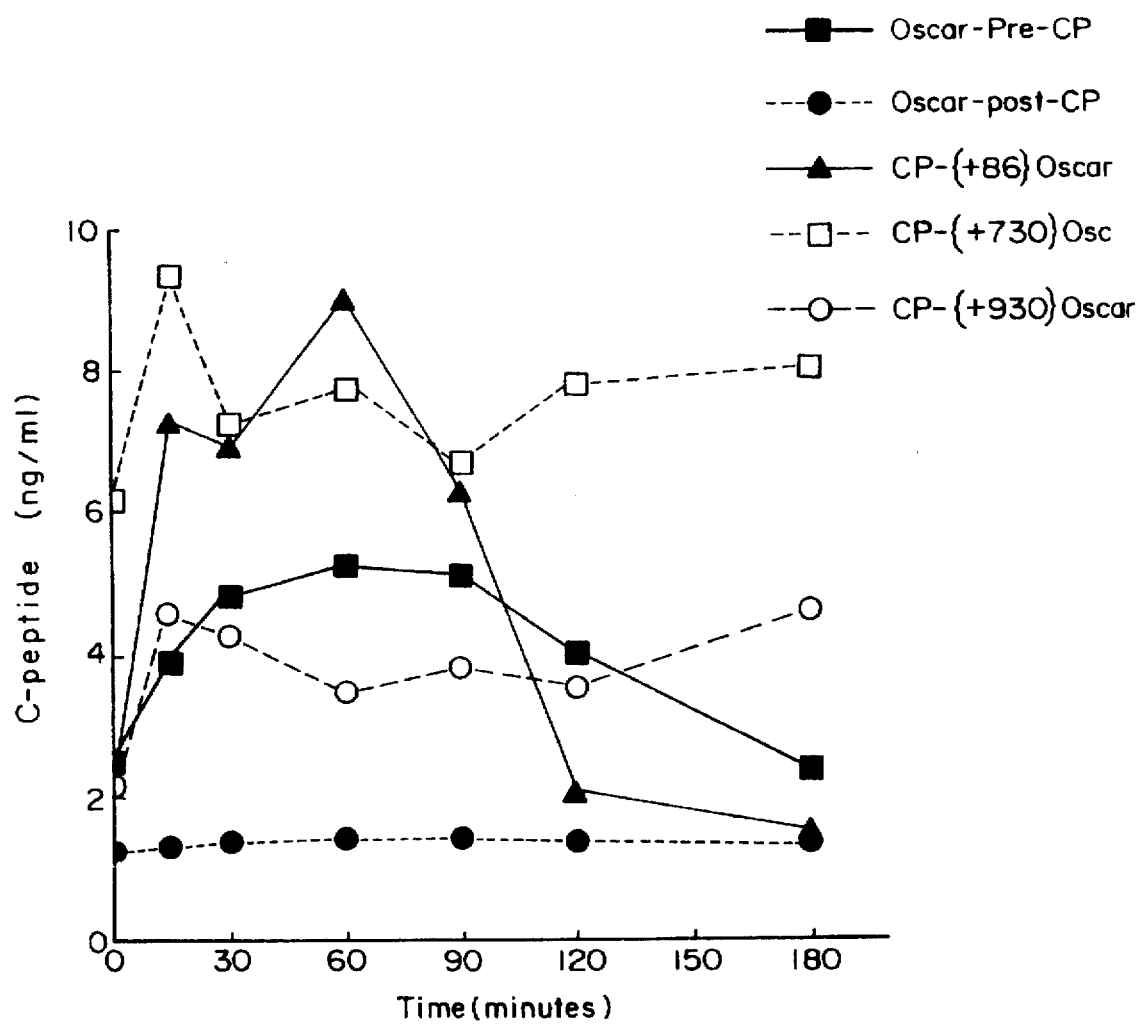
FIG. 4 shows the C-peptide responses in the same animal and at the same intervals depicted for FIG. 3.

FIG. 4 shows the C-peptide responses in the same animal and at the same intervals depicted for FIG. 3. The animal became very diabetic following the removal of his pancreas and shows blunted C-peptide responses as a result. Following transplantation and for the next 730 days the C-peptide responses were greater compared with the normals. On day 930 following transplantation the C-peptide responses have become somewhat less compared with the normals. Despite somewhat lower C-peptide levels the animal remains normoglycemic.

This example demonstrates that primates can be successfully transplanted with intratesticular islet allografts without the need for sustained immunosuppression, and that functional integrity of intratesticular islet allografts is maintained for periods exceeding two years with no evidence of graft failure.

EXAMPLE 2

This study examined insulin and glucagon secretory patterns in spontaneously diabetic bb/Wor dp rats transplanted with abdominal, intratesticular, islet grafts. Diabetic, BB/Wor dp, rats received intratesticular islet grafts from MHC-compatible BB/Wor dr rats and no immunosuppression. After a period of 74±15 days, of normoglycemia, three different groups (controls; BB/Wor dp, transplanted; and BB/Wor dp, insulin treated) were given the following challenges; (1) an oral glucose tolerance test (OGTT), (2) a single oral dose of glipizide, followed by an OGTT, and (3) arginine, by intravenous infusion. The results of this study are shown in Tables 1 and 2 and FIGS. 5 and 6.

TABLE 1

Metabolic Parameters and Immunoreactive Serum Insulin and Glucagon Levels in Control, and in Transplanted and Insulin treated, BB/Wor dp Rats.

| | | BB/Wor dp | |
|---|---|---|---|
| | Controls | Grafted* | Insulin treated |
| Plasma Glucose (mg/dl): | | | |
| Prior to therapy | 112 ± 5 | 502 ± 8+ | 510 ± 13+ |
| After 2.5 months | 197 ± 4 | 110 ± 3 | 350 ± 40 # |
| Duration p.t. OGTT (days) | 75 ± 6 | 70 ± 11 | 78 ± 19 |
| Weight gain (g) | 120 ± 6 | 105 ± 17 | 48 ± 14 $ |
| Fasting Plasma Insulin (uU/ml) | 21.9 ± 3 | 20.4 ± 2 | ND |
| Fasting Plasma Glucagon (pg/ml) | 37.8 ± 5.7 | 43.4 ± 4.6 | 47.4 ± 4.9 |

*Duration of normoglycemia after grafting (days) = 279 ± 25;
+ P <0.0001 vs. control
# P <0.0001 vs grafted;
$ P <0.02 vs. grafted

TABLE 2

Pancreatic and Testicular Insulin and Glucagon Content in Control, and in Transplanted and Insulin Treated, BB/Wor dp, Rats.

| | | BB/Wor dp | |
|---|---|---|---|
| | Controls | Grafted* | Insulin treated |
| Pancreas (mg) | 1573 ± 171 | 757 ± 122 | 920 ± 32 |
| Insulin (ug/g) | 66 ± 5.03 | 0.58 ± 0.18 | 0.76 ± 0.12 |
| Glucagon (ng/mg) | 4.1 ± 0.35* | 4.9 ± 0.33** | 6.9 ± 0.80 |
| Testes fractions: (mg) | 493 ± 49.6 | 582 ± 59.2 | 430 ± 28.0 |
| Insulin (ug/g) | 0.0 | 59.70 ± 0.49 | 0.0 |
| Glucagon (ng/mg) | 0.0 | 1.4 ± 0.37 | 0.0 |

*P <0.03 and **P <0.08, vs. diabetic, respectively

Figure 5B:
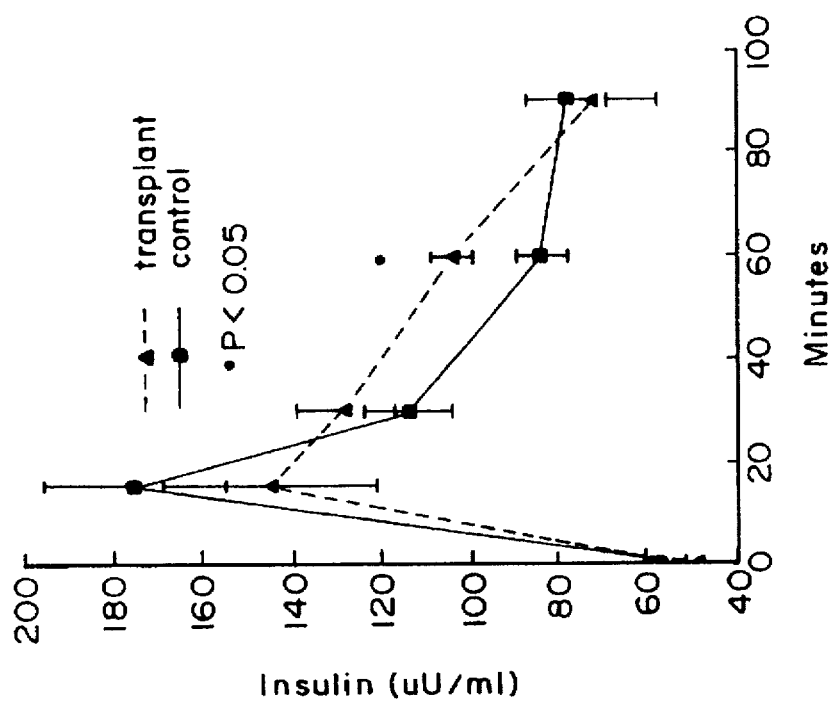
FIGS. 5a and 5b show the effect of intratesticular islet allografts on serum glucose levels and the insulin responses to oral glucose in spontaneously diabetic BB/Wor dp rats.
Figure 5A:
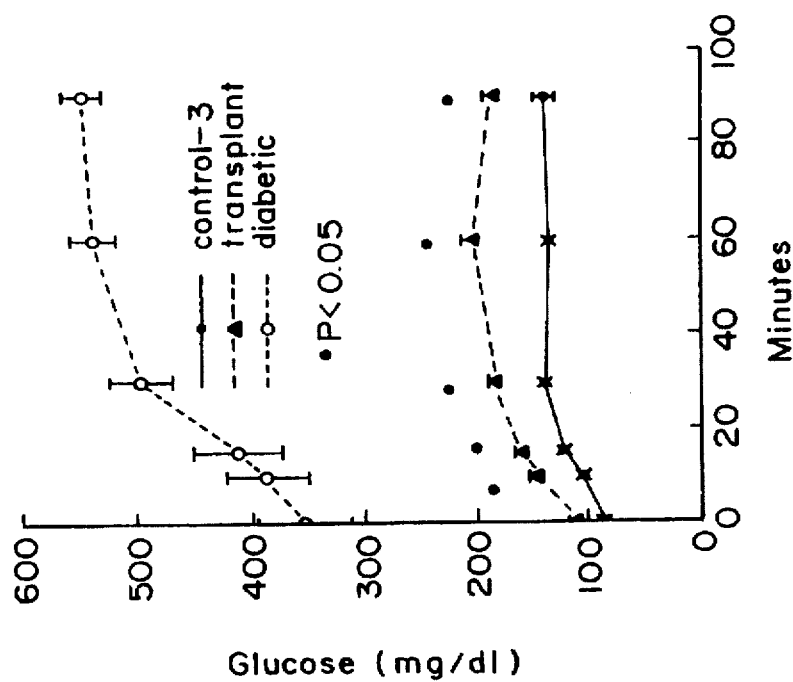
Figure 6B:
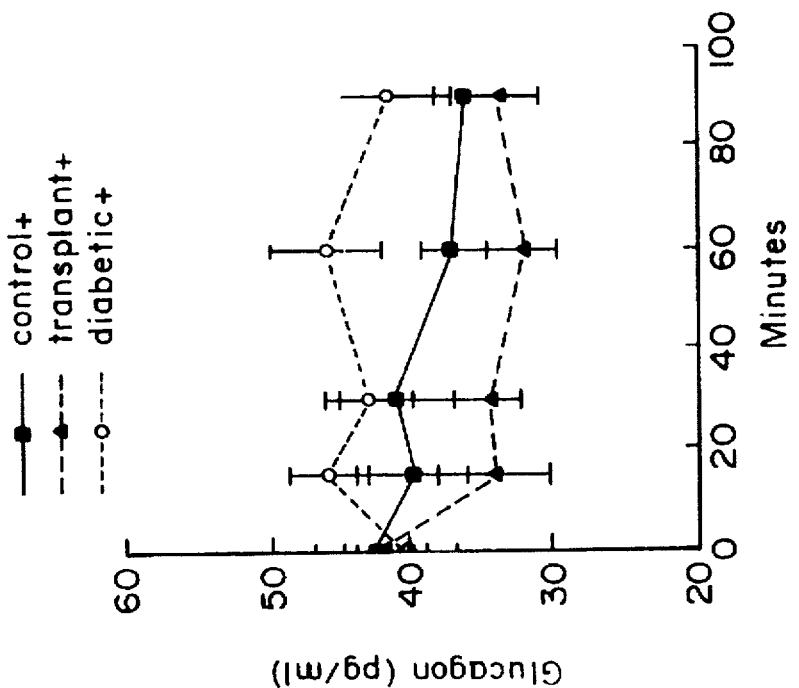
FIGS. 6a and 6b show the effect of intratesticular islet allografts on plasma glucagon secretory responses to oral glucose and a combination of glucose plus glipizide in spontaneously diabetic BB/Wor dp rats.
Figure 6A:
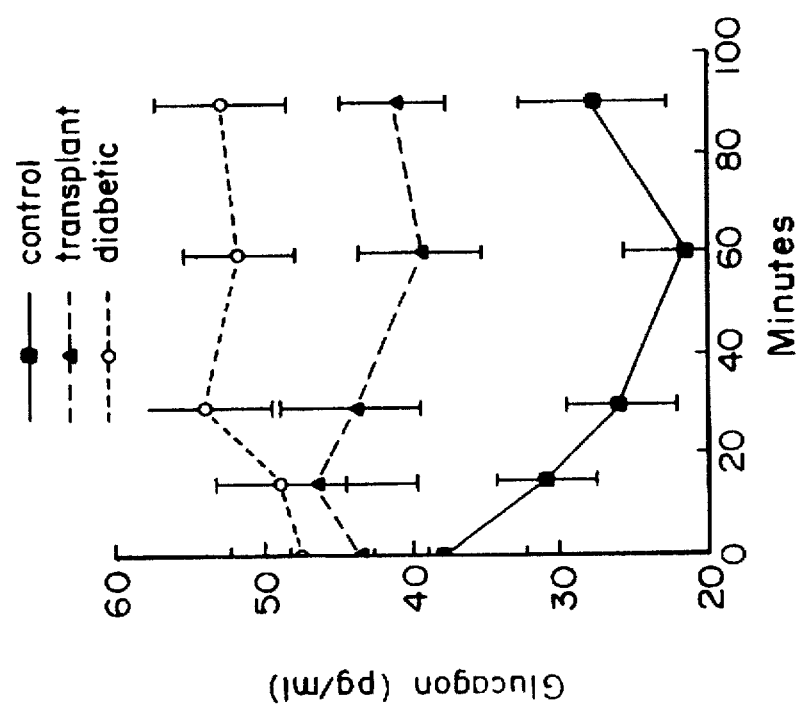

FIG. 5 shows the effect of intratesticular islet allografts on serum glucose and insulin responses to oral glucose in spontaneously diabetic BB/Wor dp rats. FIG. 6 shows the effect of intratesticular islet allografts on plasma glucagon secretory responses to oral glucose and a combination of glucose plus glipizide in spontaneously diabetic BB/Wor dp rats. This experiment demonstrates that grafted testes in spontaneously diabetic BB/Wor dp rats contain both alpha and beta cells, and that the alpha and beta cells have the capacity to respond to specific secretagogues independently.

EXAMPLE 3

This study investigated the effect of Sertoli cell-enriched fraction (SEF) on islet allograft survival in the renal subcapsular space of diabetic rats.

The animals used in this study were PVG rats, weighing between 150–200 g. Diabetes was induced by means of a single intravenous injection of 65 mg/dL of streptozotocin. Only rats with plasma glucose levels in excess of 400 mg/dL were transplanted. Sprague Dawley (S–D) outbred rats were used as islet donors. Either PVG or S–D male rats between 16 and 18 days old were used as Sertoli cell donors.

Islet Preparation

Islets were prepared according to modification of the method of London et al. (1990) *Transplantation*, 49: 1109–1113. The islets were purified on Ficoll gradients, and the isolated cells were then incubated for 4 days at 37° C. in a humidified atmosphere of 5% $CO_2$ and air prior to use. No special efforts were made to deplete the islets of contaminating passenger leukocytes.

Sertoli Cell-enriched Fraction Preparation

Highly purified preparations of Sertoli cells were isolated form the testes of young males according to the method of Cheng et al. *J. Biol. Chem.*, 26:12768–12779. The testes were removed, chopped into several pieces, and placed in a 50 mL conical tube containing 50 mL of Ham's F12/DMEM media. The pieces were washed once by centrifugation at 800×g for 2 min. The supernatant was aspirated, and the tissue resuspended in 40 mL of media containing 40 mg trypsin and 0.8 mg DNase in a sterile 250 mL Erlenmeyer flask. The flask was placed in 37° C. oscillating incubator at 60–90 osc/min for 30 min. This step removed Leydig cells. The tubules were then transferred to a 50 mL conical tube, and centrifuged at 800×g for 2 min. The supernatant fraction was aspirated, and the pellet resuspended in 40 mL of 1M glycine, 2 mM EDTA containing 0.01% soy bean trypsin inhibitor and 0.8 mg DNase, and incubated at room temperature for 10 min. This step lysed any residual Leydig cells. The cells were washed by centrifugation for 2 min, and the step repeated twice, or until the media was no longer cloudy. The pellet was resuspended by gentle homogenization with a glass Pasteur pipet in 40 mL of media containing 20 mg collagenase in an Erlenmeyer flask, and incubated at 37° C. for 5 min with 60–90 osc/min. The cell suspension was centrifuged at 800×g for two min, and the pellet resuspended by gentle homogenization with a Pasteur pipet in 40 mL media containing 40 mg collagenase and 0.2 mg DNase, and incubated in an Erlenmeyer flask at 37° C. for 30 min with 60–90 osc/min. The cells were then washed by centrifugation for 2 min, and the process repeated at least three times to eliminate peritubular cells. The cells were resuspended by gentle homogenization with a Pasteur pipet in 40 mL media containing 40 mg hyaluronidase and 0.2 mg of DNase, and incubated at 37° C. for 30 min with 60–90 osc/min. The cells were pelleted by soft centrifugation for 2 min, and washed at least five times to eliminate germ cells. The resultant SEF was resuspended in 0.25 mL of media, and immediately transplanted into the recipient rat. Each grafted rat received the equivalent of the total amount of Sertoli cells contained in a single testis.

Transplantation of Rats

The diabetic rat was anesthetized with methoxyflurane USP in a sterile hood and the left flank opened to expose the kidney. The Sertoli-enriched fraction containing approximately 5 million Sertoli cells was injected first underneath the renal capsule. The cells could be seen as a milkish bubble underneath the capsule. Immediately afterwards, a total of 10 islets/g of body weight was injected to the same milkish bubble. The needle was retracted slowly to prevent leakage of the grafted cells. Cyclosporine (CsA) was administered subcutaneously in varying doses over a 20-day period to groups two and four. Because the grafted rats responded similarly whether the drug was administered over a 20-day, or over a 3-day period, all of the subsequent groups, including the female rats, were treated with only three injections of 25 mg/kg CsA, given on days 0, +1, and +2, relative to the graft. The rats received no other therapy.

A total of 36 male and 21 female PVG rats were divided into six different treatment groups: Group 1, the control group, consisted of 6 male rats grafted with only islets from S–D donor rats. They received neither SEF nor CsA. Group 2 consisted of 10 rats grafted with a combination of islets from S–D rats and CsA postransplantation, but no SEF. Group 3 consisted of a total of 10 rats grafted with a combination of islets from S–D and SEF from PVG donor rats, but no CsA postransplantation. Group 4 consisted of 10 rats grafted with a combination of islets from S–D donors, SEF from PVG donors, and CsA postransplantation. Group 5 consisted of 11 female rats grafted with the same combination of cells as depicted for Group four. Group 6 consisted of 10 female rats grafted with a combination of islets and SEF, both cell types from S–D donors, and CsA postransplantation.

Postransplantation Evaluation of Rats

The grafted rats were transferred to metabolic cages, and plasma glucose levels were obtained at weekly intervals. Urine volumes and urine glucose contents were obtained at daily intervals. A rat was considered cured of the diabetic process if the following criteria were met: A random plasma glucose level ≦150 mg/DL; glycosuria; and immediate reversal to hyperglycemia following surgical removal of the grafted kidney.

To determine if any of the rats had become unresponsive to their grafts, normoglycemic rats were challenged with a secondary islet allograft consisting of at least 500, freshly prepared, Sprague Dawley islets which were injected into the contralateral renal subcapsular space. No immunosuppression was given following the challenge.

To examine the impact of the transplantation of SEF on fertility of the female rats, normoglycemic animals of longer than 30 days were mated with PVG males. Metabolic parameters, as outlined above, were closely monitored, as was the course of their pregnancies.

Structural Analysis of Grafted Tissue

A total of five successfully grafted rats were nephrectomized at intervals following transplantation. Wedge sections of renal tissue, obtained from sites at which islets and SEF had been injected, were prepared for examination by light and electron microscopy, as previously described by Cameron et al. (1990) *Transplantation*, 50:649–653. Briefly, the tissue wedges were immersion-fixed with 5% glutaraldehyde in 0.1M s-Collidine buffer for 1 h, washed in buffer, and post-fixed for 1 h with 1% osmium tetroxide in 0.1M buffer. Small tissue blocks were cut from the wedges, and dehydrated through a graded series of ethyl alcohols, transferred to propylene oxide, and embedded in Epon 812/Araldite plastic resin. Thick (0.5 µm) and thin (900 mg) sections were strained routinely with toluidine blue and uranil acetate/lead citrate, respectively, for structural analysis by light and electron microscopy. The results are shown in Table 3 and FIGS. 7–9.

TABLE 3

Effect of Sertoli cells on islet allograft survival in the non-immunologically privileged renal, subcapsular site

| Group (n) | Gender | Sertoli cell (donor origin) | CsA | Duration of normoglycemia (days) Individual Responses |
|---|---|---|---|---|
| 1 (6) | Male | — | — | 0, 0, 0, 0, 0, 0 |
| 2 (10) | Male | — | + | 0, 0, 0, 0, 0, 0, 0, 130 > 441, >445 |
| 3 (10) | Male | + (PVG) | — | 0, 0, 0, 0, 9, 10, 12, 13, 13, 14 |
| 4 (10) | Male | + (PVG) | + | 19, 76, 58*, 84*, 167*, 127 , 139 , >418 , >422 , >425 |
| 5 (11) | Female | + (PVG) | + | 7, 11, 14, 28, >287 , >305 , >306 , >308 , >441 , >447 , >457 |
| 6 (10) | Female | + (S-D) | + | 8, 10, 96*, 128*, >168, >172, >184, >193, >193, >196 |

*nephrectomized,
challenged with a secondary islet allograft.

Group 1:

None of the six rats grafted with islets alone, without either SEF or CsA, became normoglycemic.

Group 2:

Three of 10 rats grafted with islets and treated with CsA became normoglycemic for more than 100 days. The 3 normoglycemic rats were challenged with a secondary graft on days 116, 192 and 197, respectively. One rat reverted to hyperglycemia on day 130, while 2 remained normoglycemic.

Group 3:

Initially 6 of the 10 rats grafted with islets and SEF, but no CsA, became normoglycemic, but all of them reverted to hyperglycemia by day 14.

Group 4:

All 10 of rats grafted with a combination of SEF and islets, and also given CsA became normoglycemic. Two reverted spontaneously to diabetes on days 19 and 76, respectively. Three were nephrectomized on days 58, 84 and 167 following transplantation. All 3 of these rats became hyperglycemic within the next 24 h. The remaining 5 rats were challenged with a secondary islet allograft on days 119, 129, 280,342 and 400, respectively. Of these, the first 2 reverted to diabetes on day 127 and 139, respectively, while the latter 3 remained normoglycemic.

Group 5:

All 11 of the female rats grafted with a combination of islets and SEF, and then given CsA, became normoglycemic. Of these, 4 reverted spontaneously to hyperglycemia by day 28. Of the 7 normoglycemic rats who were mated with male PVG rats, 6 became pregnant, and of these, 8 had litters varying between 1 and 10 pups. They were able to nurse the pups successfully. A total of 7 of the long-term surviving females were challenged with secondary islet allografts at least 200 days following transplantation. None of them reverted to hyperglycemia.

Group 6:

Of the 10 rats grafted with islets and SEF from the same donor strain of rat, all 10 became normoglycemic. Two reverted to hyperglycemia by day 10. A nephrectomy to remove the graft was done on 2 of the long-term surviving rats on days 96 and 201, respectively. Both reverted to hyperglycemic immediately within the next 24 h.

Tissue Morphology

Figure 7:
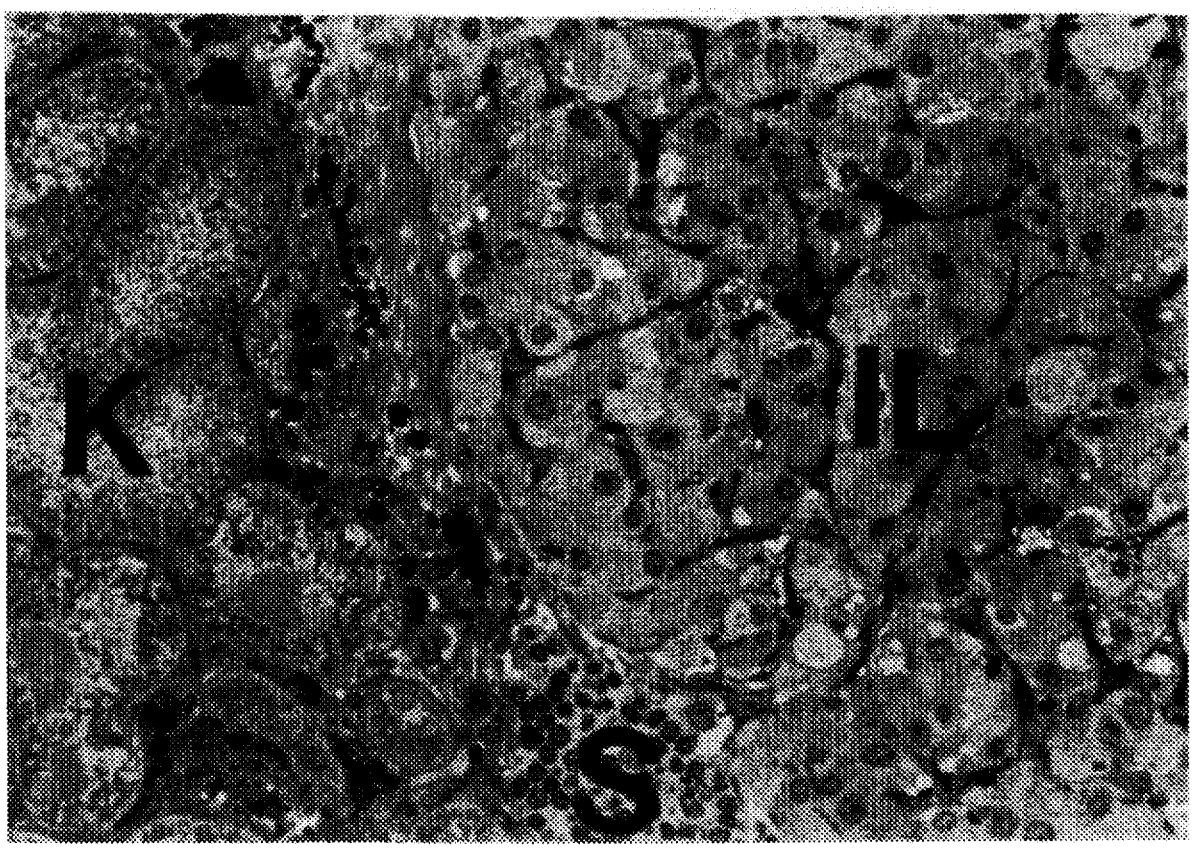
FIG. 7 shows a light micrograph of the pancreatic islets of Langerhans and the isolated rat Sertoli cells transplanted into the renal subcapsular space of a diabetic rat.
Figure 8:
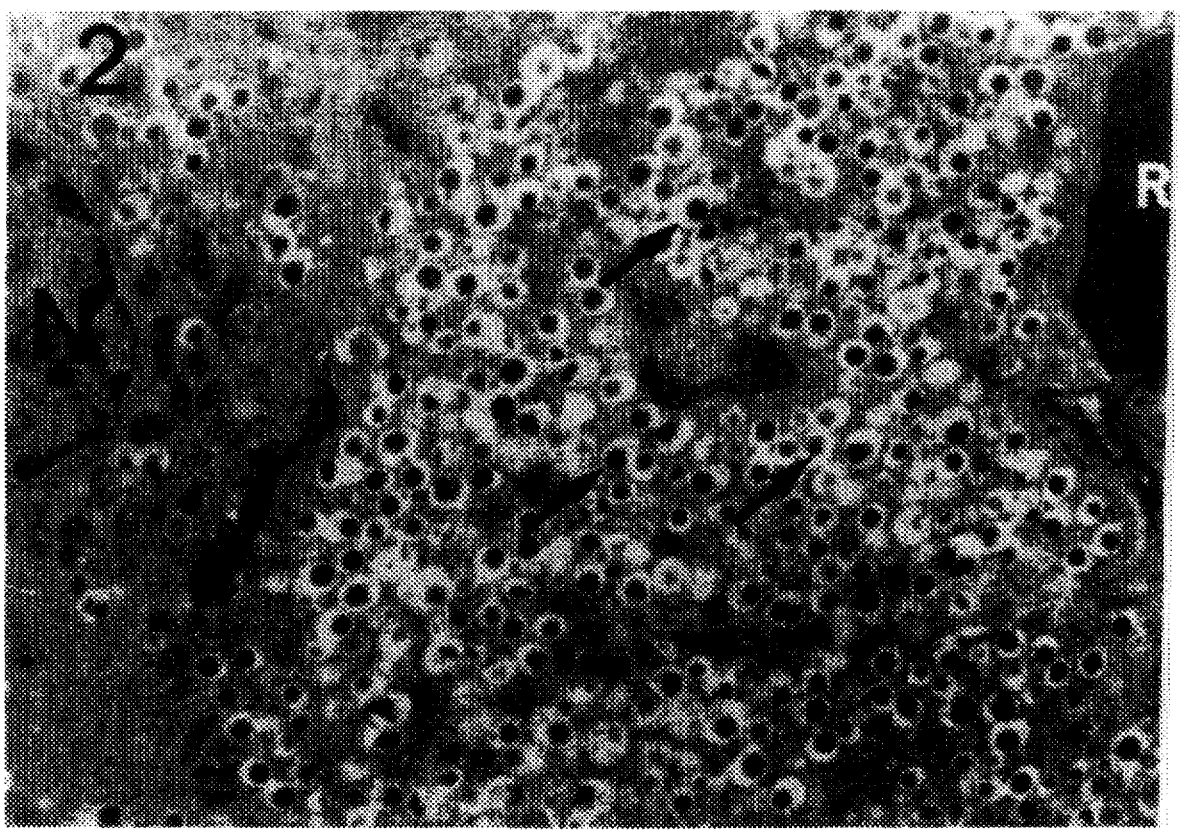
FIG. 8 shows an electron micrograph of an individual cell within the transplanted islet.

Renal tissue obtained from the long-term grafted kidney appeared structurally normal by light microscopy (FIG. 7). Transplanted islets in this organ were immediately subjacent to the kidney capsule, and also appeared structurally normal. They displayed tissue and cellular architecture identical to islets in situ (FIG. 7). Individual islet cells were partitioned into cell clusters by thin connective septa containing small vessels and capillaries (FIG. 7). It appeared that most of the islet cells contained secretion granules. When resolved by electron microscopy, islet cells were identified as the β-cell type by the inclusion of ultrastructurally distinctive, and unique insulin-containing secretion granules (FIG. 8). All β-cell clusters observed were in close proximity to intra-islet capillaries (FIG. 8).

Figure 9:
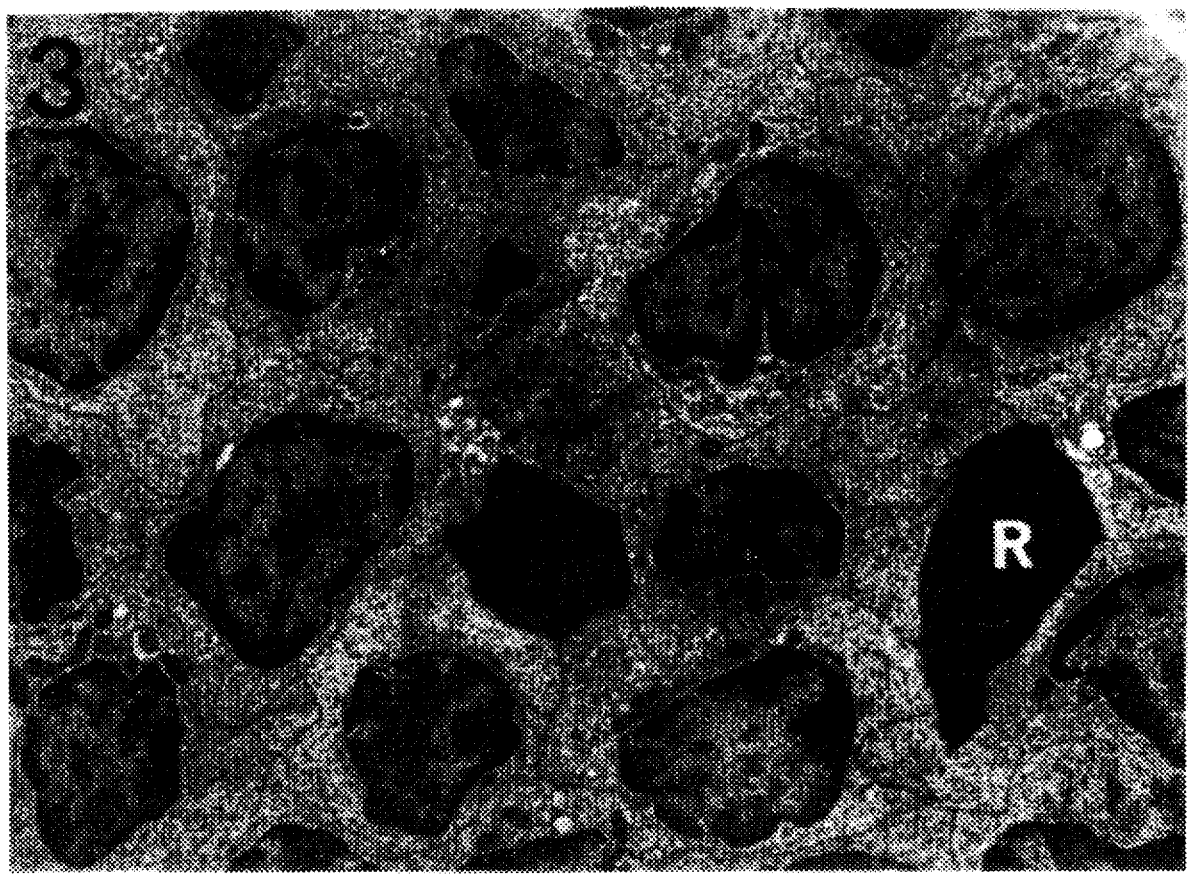
FIG. 9 shows an electron micrograph of the fine structure of the extra-islet cells labeled "S" in FIG. 7.

There was a high density of cells between, and directly adjacent to, the transplanted islets and renal parenchyma. By light microscopy, they did not appear to be islet cells, kidney cells nor cells or blood origin (FIG. 7). When observed by electron microscopy, these cells were similar in ultrastructure to Sertoli cells in that their nucleic were irregular in profile, and contained deep nuclear clefts, distinctive nucleoli were often present, and mitochondrial structure was dense. Although these cells did not retain the typical polarity of Sertoli cells in vivo, they were, however, identical in appearance to Sertoli cells in vitro, when the cells are not plated on a basement membrane substrate. The cells were not associated with a basement membrane, and appeared randomly organized (FIG. 9). Cells showing ultrastructural features of either germ or Leydig cells were not observed.

This example demonstrates that an immunologically privileged site for transplantation of isolated islet can be created in male and female diabetic recipients by transplantation of Sertoli cells without the need for sustained immunosuppression.

EXAMPLE 4

This study determined the survival of discordant islet xenografts in various nonimmunologically privileged organ sites in experimental animals.

Islets were prepared from young piglets as follows: Male piglets not weighing more than 2.2 kg were used exclusively. The piglet was anesthetized and following exsanguination both pancreas and testes were harvested under sterile conditions. A collagenase solution consisting of 2 mg/ml of collagenase type XI (Sigma) was injected directly into the pancreas. The pancreas was incubated at 37° C. for 17 minutes and the digested tissues washed three times by means of centrifugation and aliquots of 1 ml each transferred to Petri dishes. The islets were incubated at 32° C. in tissue culture media 199 supplemented with 10% horse serum for six days.

On day seven the cultured islets were collected in batches of ±4,000 and cryopreserved using a standard protocol. The cells were stored in liquid nitrogen at −96° C. for periods varying between two and four weeks. The islets were removed from the liquid nitrogen and thawed using an established procedure. The thawed islets were transferred to Petri dishes and co-cultured with pig Sertoli cells for three days at 32° C. in the same 199 culture media as described above. Earlier studies have shown an improved survival rate of thawed islets cultured in the presence of Sertoli cells.

On day three following thawing the islets were hand-picked and counted and a total amount of 12 islets/g of body weight transplanted into female diabetic Sprague Dawley rats. A total of 5 million Sertoli cells procured from the piglet testes were grafted simultaneously into the same location. The organ sites to be tested for the grafting of islets include: a] the renal subcapsular space, b] subcutaneously, and c] the liver. Following transplantation, the rats were treated with cyclosporine as follows: 25 mg/kg for 7 days; 15 mg/kg for 5 days; 10 mg/kg for 5 days; 5 mg/kg for an additional 13 days. On day 30 the drug was discontinued.

To demonstrate viability and functional integrity of isolated piglet islets the following studies were done: a) staining of Cells with dithizone, a stain which is highly specific for insulin; b) staining of cells with 0.4% trypan blue which indicates viability of the islets; and c) culturing of batches of 5 islets in the presence of insulin secretagogues such as low and high glucose concentrations at specified intervals following culturing, cryopreservation and thawing. The results are shown in Table 4.

TABLE 4

Insulin secretion (micro-units/ml) from incubated and from cryopreserved-thawed islets done on days 3, and 7, and 14, of culturing, respectively.

| | Micro-units of Insulin release per 5 Islets Days following isolation and incubation | | |
|---|---|---|---|
| | 3 Days | 7 Days | 14 Days |
| Incubated islets prior to cryopreservation: | | | |
| a] Low glucose (90 mg/dl) | 15.3 ± 3.8 | 21.8 ± 1.1 | 17.29 ± 2.4 |
| b] High glucose (300 mg/dl) | 32.2 ± 5.4 | 37.14 ± 3.4 | 23.3 ± 1.8 |
| Cryopreserved and thawed islets | | | |
| a] Low glucose (90 mg/dl) | 14.52 ± 2.8 | 7.13 ± 1.3 | 5.38 ± 2.02 |
| b] Low glucose + Sertoli cells | 10.31 ± 2.8 | 9.17 ± 2.6 | 8.38 ± .41 |

TABLE 5

Yield of porcine islets following 1, 3, and 7 days of culture and the percentage of islets lost during 7 days of culture.

| Fig. No. | BW (kg) | Panc W g | D1 islets/ g panc | D3 islets/ g panc | D7 islets/ g panc | islet loss % D7/D1 |
|---|---|---|---|---|---|---|
| 1 | 1.6 | 1.79 | 36,536 | 31,659 | 27,212 | 26% |
| 2 | 2.0 | 1.89 | 37,272 | 32,962 | 27,883 | 25% |
| 3 | 2.3 | 2.46 | 29,268 | 26,046 | 20,884 | 29% |
| 4 | 1.8 | 1.66 | 39,904 | 37,726 | 31,664 | 21% |
| 5 | 1.8 | 1.76 | 37,846 | 34,578 | 3D,046 | 21% |
| 6 | 1.6 | 1.74 | 39,866 | 37,888 | 32,424 | 19% |
| 7 | 1.4 | 1.61 | 42,126 | 39,456 | 33,872 | 20% |
| 8 | 2.3 | 2.48 | 33,682 | 29,334 | 24,892 | 26% |
| 9 | 2.1 | 2.28 | 43,478 | 41,226 | 37,394 | 14% |
| 10 | 2.1 | 2.09 | 40,126 | 36,448 | 33,282 | 17% |
| 11 | 2.1 | 2.12 | 31,248 | 27,170 | 26,415 | 15% |
| 12 | 2.1 | 1.98 | 38,848 | 36,465 | 29,293 | 25% |
| 13 | 2.2 | 2.06 | 39,146 | 37,446 | 31,709 | 19% |
| 14 | 2.2 | 2.24 | 27,892 | 25,028 | 21,342 | 23% |
| 15 | 2.7 | 2.69 | 44,610 | 38,364 | 31,524 | 29% |
| 16 | 1.5 | 1.44 | 42,222 | 40,414 | 31,244 | 26% |
| Mean ± SE | 2.0 ± 0.3 | 2.0 ± 0.4 | 37692 ± 1233 | 34513 ± 1307 | 29442 ± 1119 | 22.2 ± 1.2% |

TABLE 6

Recovery of islets following freezing and thawing in presence and absence of Sertoli cells

| No. of islets | Islets alone | | | Islets + Sertoli cells | | |
|---|---|---|---|---|---|---|
| | Pre-cryo | Post thawing | Recovery (%) | Pre-cryo | Post thawing | Recovery (%) |
| D3F/D3T | 250 | 152 | 61% | 290 | 212 | 73% |
| | 230 | 131 | 57% | 260 | 228 | 88% |
| | 440 | 278 | 63% | 430 | 380 | 88% |
| | 420 | 365 | 87% | 410 | 324 | 79% |
| | 450 | 290 | 64% | 440 | 358 | 81% |
| | Means | | 66.4% | | | 81.8% |
| D7F/D3T | 260 | 136 | 52% | 250 | 229 | 92% |
| | 300 | 208 | 69% | 300 | 202 | 67% |
| | 280 | 177 | 63% | 290 | 238 | 82% |
| | 360 | 205 | 57% | 350 | 300 | 86% |
| | 320 | 218 | 68% | 390 | 289 | 74% |
| | 380 | 217 | 57% | 320 | 270 | 84% |
| | Means | | 61.0% | | | 80.8% |

As shown in Table 5, the yield of islets per gram pancreas was 37692±1233, 34513±1307 and 29,442±1119, after 1, 3 and 7 days of culture, respectively. Following cryopreservation and thawing and reculturing of the cells in the presence of Sertoli cells approximately 20% of the cells were damaged or lost as shown in Table 6. Thus ±24,000 islets/gram of piglet pancreas were available for transplant purposes after cryopreservation and thawing.

The results showed that insulin secretion was blunted when glucose was used as insulin secretagogue prior to cryopreservation. The effect was more evident following cryopreservation and thawing. While the presence of Sertoli cells had marked effects on number of islets that survived cryopreservation and thawing their presence had little effect on the ability of the islets to respond to a low glucose concentration as insulin releasing agent. However, as shown in Example 8 the presence of Sertoli cells augmented the secretion of insulin in the presence of high glucose concentrations and glucose plus Forskolin.

EXAMPLE 5

Response of Diabetic Sprague Dawley Rats to the Transplantation of Islets from Piglet Donors (Discordant Xenografts)

The rats were made diabetic by means of a single i.v. injection of 55 mg/kg of streptozotocin. They were grafted only if the blood sugar was equal to or more than 400 mg/dl. Following transplantation the rats were placed individually in metabolic cages and urine volume, urine glucose content, and body weights were measured at daily intervals. Blood glucose levels were done at weekly intervals. A rat is considered cured of diabetes if the blood glucose level is 160 mg/dl or less and/or the daily urine volume is 15 ml or less.

Figure 10:
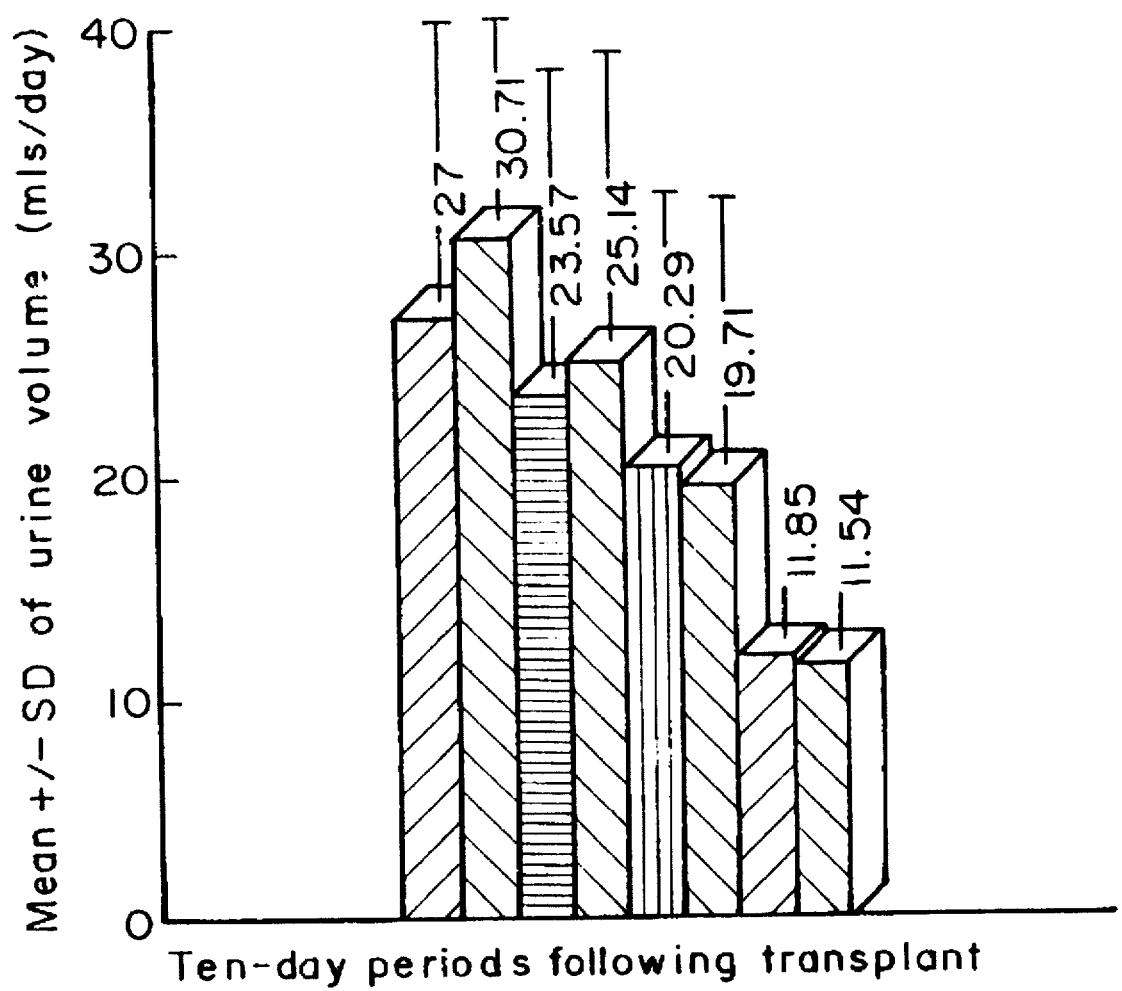
FIG. 10 shows the effect of transplantation of piglet islets and Sertoli cells underneath the renal capsule on the mean daily urine output of seven grafted female rat recipients. Each bar represents the mean daily urine output over a ten-day period following transplantation.
Figure 11:
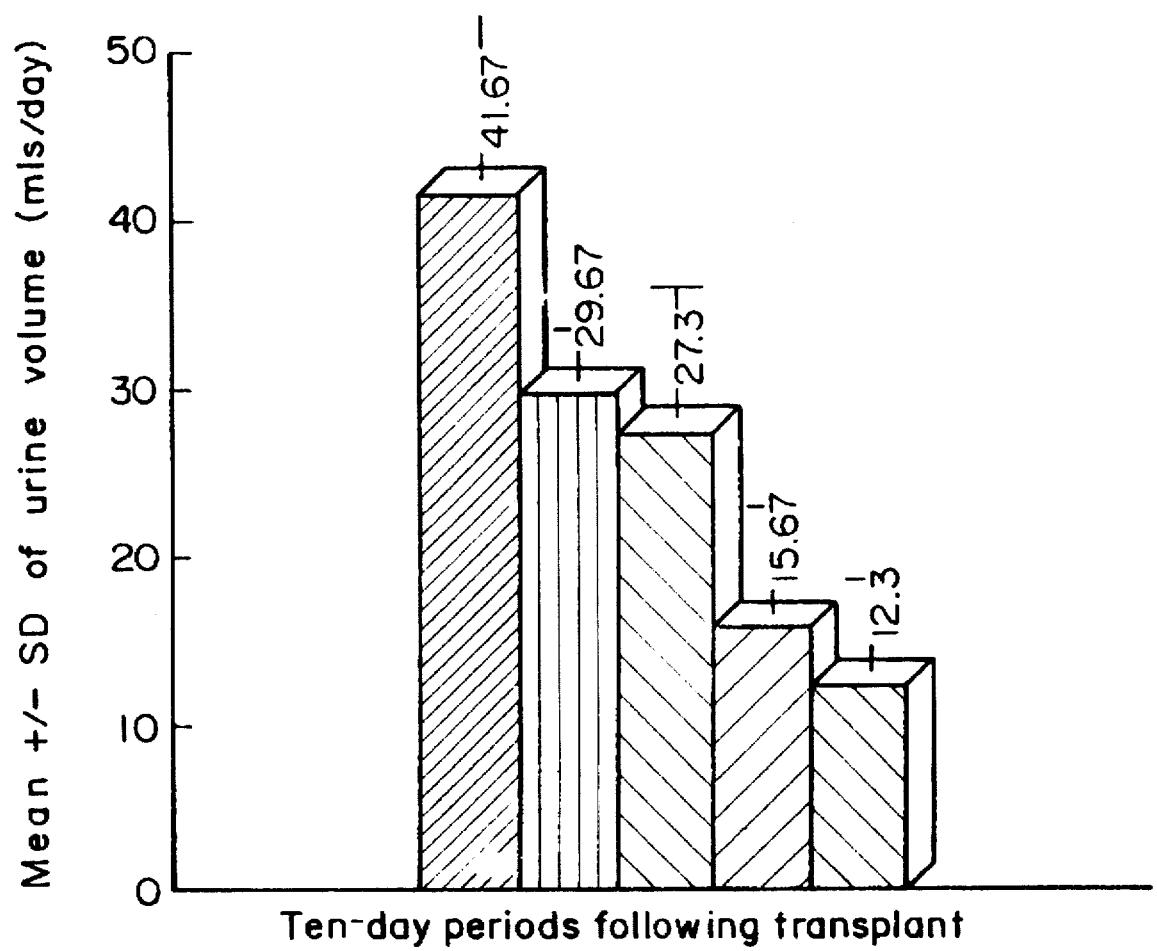
FIG. 11 shows the effect of the transplantation of piglet islets and Sertoli cells underneath the skin on the mean daily urine volumes of three rats over a 50-day period.
Figure 12:
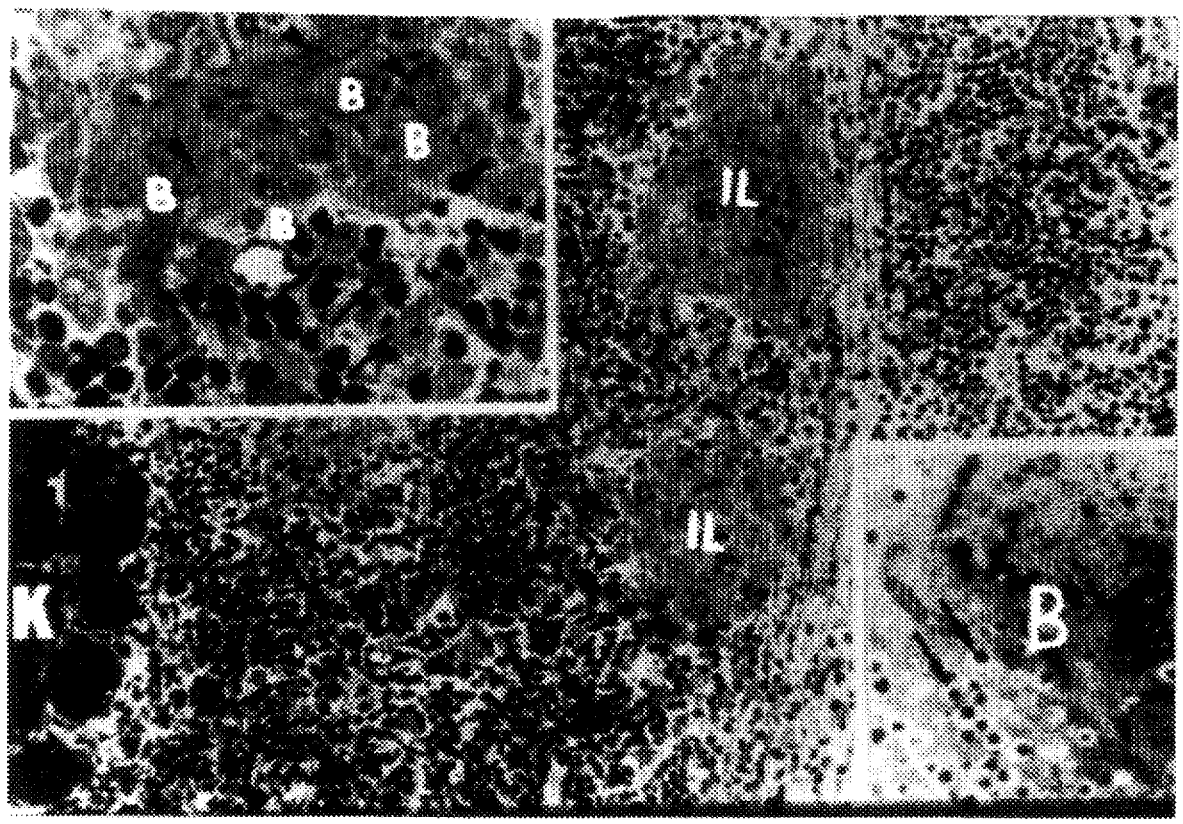
FIG. 12 shows the light photomicrograph of pig islets of Langerhans and rat Sertoli cells transplanted into the renal subcapsular space of a diabetic rat. IL shows the presence of islands of beta cells (IL) surrounded by an infiltration of small lymphocytes underneath the renal capsule (K); B (upper left) shows at higher magnification that the islands (IL) consist of beta cells and B (lower right) shows that beta cells contain characteristic insulin granules.

The results are illustrated in FIGS. 10 and 11.

FIG. 10 shows the effect of transplantation of piglet islets and Sertoli cells underneath the renal capsule on the mean daily urine output of seven grafted female rat recipients. Each bar represents the mean daily urine output over a ten-day period following transplantation. The study has been conducted over an 80-day period, the bar on the furthest right thus showing the mean urine output per day from day 80 through 89, etc.

The figure shows that the mean daily urine volume for the first 60 days varied between 19.7 mls and 27 mls or within a diabetic range. It can be readily appreciated that urine volumes decreased to near-normal levels only from days 70 through day 89. The corresponding plasma glucose levels during the first and last then day periods were 474±46 and 155±70, mg/dl, respectively.

These results indicate that following transplantation with piglet islets and Sertoli cells the rats showed evidence of survival of the grafted islets. The reversal to normoglycemia took about 80 days.

It should be noted that one of the cured rats is pregnant and has been normoglycemic throughout her pregnancy.

FIG. 11 shows the effect of the transplantation of piglet islets and Sertoli cells underneath the skin on the mean daily urine volumes of three rats over a 50-day period. The results show that the mean urine volume decreased from a mean of 41.7 ml during the first 10-day period to an average of 12.3 mls during the fifth week. The corresponding glucose levels were 509±45, and 200±12, mg/dl, respectively.

The data depicted above demonstrate that both the renal subcapsular space and the subcutaneous area can be used as a site to create an immunologically privileged site for the transplantation of islet xenografts.

EXAMPLE 6

This study determined the effect of cultured Sertoli cells on the survival of discordant islet xenografts in diabetic rats with minimal early exogenous immunosuppression.

Preparation of Islets

Neonatal piglets of less than seven days of age were killed by anesthesia and islets were isolated according to a method of Kuo C. Y., Burghen G. A., Myvacle A. and Herrod H. G. (1994) "Isolation of islets from neonatal pig pancreatic tissue", J. Tissue Culture Methods, 16:1–7. Briefly, the pancreas was distended by an injection of a collagenase solution, 2 mg/ml, collagenase type X1, in culture medium DMEM. After incubation at 39° C. for 17 min, the digested fragments were washed by centrifugation and the digested tissue was then incubated for one week in medium 199 supplemented with 10% horse serum and 1%, anatibiotics at 32° C. The islets were then cryopreserved according to the method by Lakey J. R. T., Warnock G. L., Kneteman N. M., Ao Z., Rajotte R. V. (1994) "Effects of pre-cryopreservation culture on human islet recovery and in vitro function", Transplant Proc., 26:820 and stored in liquid nitrogen at −196° C. Three days prior to transplantation the cryopreserved islets were rapidly thawed and cultured at 32° C. for two days. One day prior to transplantation some of the islets were collected and co-cultured with Sertoli cells for 24 hours.

Sertoli cell isolation

Testes of young S–D rats were removed and Sertoli cells were isolated by the method of Cheng C. Y. and Bardin C. W. (1987) "Identification of two testosterone-responsive proteins in Sertoli cell-enriched culture medium whose secretion is suppressed by cells of the intact seminiferous tubule." J. Biol. Chem., 262:12768–12779. Briefly, the testes were digested first in DMEM containing 1.0% trypsin, and then is DMEM containing 1.0% collagenase, type 1, for periods of 15 min each, at 37° C. The purified Sertoli cells were cultured at 37° C. in DMEM/F12 supplemented with transferrin, 10 ug/ml, FSH 10 ng/ml, insulin 20 ug/ml and 1.0% FCS, for three days. For transplantation, Sertoli cells and islets were pooled and rats were grafted with either a composite consisting of 5×10$^6$ Sertoli cells and 3,000 islets, or with islets alone (15 islets/g of body weight).

Transplantation of rats

Female S–D rats, weighing between 170 and 200 g were made diabetic by means of a single i.v. injection of 60 mg/kg of streptozotocin. A total of 31 diabetic rats were divided into 3 groups and grafted as follows: Group 1, a control group (n=8), received a total of 15 islets/g body weight injected underneath the renal capsule. No Sertoli cells were grafted. Following transplantation the rats were treated with cyclosporine for 55 days: 25 mg/kg for 3 days, 15 mg/kg for 10 days, 10 mg/kg for 10 days and 5 mg/kg for the following 32 days. Immunosuppression was then stopped. Each rat received, in addition, 1–3 U of Ultralente insulin at daily intervals if the 24-hour urine glucose content exceeded 1 g. Insulin therapy was stopped on day 55. Group 1, a tissue control group (n=8), was given a renal, subcapsular injection of a composite of about $5 \times 10^6$ Sertoli cells and 3,000 islets. No CsA was given. Insulin was given as depicted above. Group 3, the experimental group (n=15), was transplanted with both Sertoli cells and islets and then treated with CsA and insulin according to the schedule outlined above.

Postransplantation evaluation of rats

Plasma glucose levels were obtained at weekly intervals. Twenty four hour urine volumes and urine glucose contents were recorded daily. A rat was considered cured of the diabetic process if the following criteria applied: A plasma glucose level of equal to or less than 10 mmol/L, a 24-hour urine volume of less than 15 ml, and immediate reversal to hyperglycemia following surgical removal of the grafted kidney. One normoglycemic rat was mated on day 69 to test her ability to become pregnant.

Structural analysis of the grafted tissue

Two normoglycemic rats were nephrectomized on days 117 and 330 and grafted tissue prepared for light and electron microscopy. Selawry H. P., Cameron D. F. (1992) "Sertoli cell-enriched fractions in successful islet cell-transplantation", Cell Trans., 2:123–129. Briefly, tissue wedges were immersion-fixed with 5% glutaraldehyde in 0.1M collidine buffer for 1 h., washed in buffer, and post-fixed for 1 h with 1% osmium tetroxide in 0.1M buffer. Small tissue blocks were cut from the wedges, and dehydrated through a graded series of ethyl alcohols, transferred to propylene oxide, and embedded in Epon 812/Araldite plastic resin. Thick (0.5 um) and thin (900 ng) sections were stained routinely with toluidine blue and urinal acetate/lead citrate, respectively, for structural analysis by light and electron microscopy.

The results of the effect of Sertoli cells and cyclosporine on survival of xenographic transplantation of pig islet cells into the renal subcapsular space of diabetic female rats are shown in Table 7.

TABLE 7

| Group (n) | Sertoli Cells | CsA | Graft Survival (days) |
| --- | --- | --- | --- |
| 1 (8) | − | + | 0, 0, 0, 0, 0, 0, 0, 0 |
| 2 (8) | + | − | 0, 0, 0, 0, 0, 0, 0, 0 |
| 3 (15) | + | + | 0, 0, 0, 0, 0, 71, 77, 96, 117\*, 148#, >154, >165, >327, 330\* |

\*rats nephrectomized to remove the xenograft
rat died during a cardiac puncture As shown in Table 7, none of the rats grafted with islets alone and then given CsA and low-dose insulin (Group 1) became significantly less hyperglycemic. Further, none of the rats grafted with a composite of islets and Sertoli cells, but without CsA, showed any improvement of hyperglycemia (Group 2). Of 15 rats grafted with islets and Sertoli cells and then given CsA (Group 3), 10 showed evidence of reversal of the diabetic state. Four of the ten are still normoglycemic for periods of more than 154, 165, 165, and 327 days, respectively. The normoglycemic rats who were nephrectomized on days 117 and 330, became hyperglycemic immediately. Their plasma glucose levels were 4.9 mmol/L, and 8.2 mmol/L, prior to, and 20.7 mmol/L, and 32.2 mmol/L, respectively, following nephrectomy. A female rat who was mated on day 69 became pregnant and delivered a total of 10 pups on day 89, all of whom she nursed successfully while remaining normoglycemic. She died on day 148 as a result of a cardiac puncture. Three of 10 rats regressed into hyperglycemia on days 71, 77, and 96, respectively, after a short period of euglycemia.

These results demonstrate that prolonged survival of a discordant islet xenograft (pig to rat) can be achieved in female diabetic rats. Survival of islet xenografts depended upon two factors which had to be administered concomitantly: Co-transplantation with Sertoli cells and treatment with cyclosporine.

The response of total urine volumes following transplantation with a composite of pig islet and rat Sertoli cells measured at 10-day intervals over an 80 day period for 7 of the improved rats showed an average daily urine volume of 27.0±13.0 ml/rat during the first 10-day period, which slowly declined to a mean of 12.0±4.0 ml/rat, 70 days following transplantation.

Tissue morphology studies shown in FIG. 10 show that the tissue and cellular structure of kidney parenchyma appeared normal in the rat nephrectomized 117 days following transplantation. Normal appearing islets with structurally distinct B-cells were visible in well vascularized areas subjacent to the kidney capsule. Additionally, normal appearing Sertoli cells were observed adjacent to the transplanted islets along with numerous lymphocytes. No plasma cells were identified at the transplantation site. Viable endocrine cells were similarly observed in the subcapsular renal space of the rat nephrectomized 330 days following transplantation.

These studies show that significant prolongation of survival of a discordant islet xenograft can be achieved without sustained immunosuppression. These studies demonstrate that the mechanism by which Sertoli cells promote islet xenograft survival is three-fold: (1) Sertoli cells stimulate the recovery of islets damaged during transplantation (i.e. improve the yield and function of cultured islets), (2) Sertoli cells protect grafted islets from immunologic rejection by producing factors which strongly suppress proliferation of T-cells, and (3) Sertoli cells protect grafted islets from the toxic effects of cyclosporine.

EXAMPLE 7

This study shows a method of isolating and cryopreserving porcine pancreatic islets for future xenographic transplants in mammals.

Male piglets, <7 days old and weighing 2±kg were used as donors. The pancreases, weighing 1.4±0.3 g, were harvested and injected with DMEM solution containing 2 mg/ml collagenase XI. The distended pancreas was incubated in a shaking water bath at 39° C. for 17 min. The digested tissue was filtered through a 500 μm stainless steal filter and filtrates were washed ×3 with cold DMEM. Without further purification the cells were cultured in M199 and 10% horse serum at 32° C. for 7 days. The islet cells were then cryopreserved using standard procedures. At specified intervals islets were thawed and cultured in M199, both in presence, and isolated from testes of male piglets according to a standard method.

To test functional capacity, islets cultured for 3 and 7 days were assessed for insulin release in static incubation. In separate experiments, effect of insulin secretagogues was tested on islets cultured with and without Sertoli cells. The results of this study are shown in Tables 8 and 9.

TABLE 8

Effect of insulin secretagogues, glucose and glucose plus Forskolin, on Insulin release from Incubated and Frozen/thawed (F/T) islets in the presence and absence of Pig Sertoli cells.

| | Insulin Release (uU/ml/10 islets) | | |
|---|---|---|---|
| | 3.3 mmol/L glucose | 16.7 mmol/L glucose | 16.7 mmol/L glucose + 100 umol Forskolin |
| Day 3 Incubated with Sertoli cells | 42.3 ± 1.2 | 112.8 ± 17.7*# | 267.7 ± 43.0**# |
| Day 3 Incubated alone | 31.3 ± 2.1 | 57.3 ± 3.8* | 123.4 ± 15.3** |
| Day 7 Incubated with Sertoli cells | 22.9 ± 1.9 | 64.5 ± 6.4*# | 153.9 ± 14.6** |
| Day 7 Incubated alone | 21.3 ± 1.2 | 37.3 ± 6.0* | 120.3 ± 11.4** |
| Day 3 F/T with Sertoli cells | 20.6 ± 4.3 | 44.9 ± 9.9* | 77.1 ± 13.7** |
| Day 3 F/T alone | 11.7 ± 2.3 | 27.9 ± 6.6* | 54.5 ± 10.7** |

Anova Test: *vs 3.3mmol/L p 0.05, **vs both 3.3 & 16.7 mmol/L P <0.05 # with sertoli cells vs islets alone P <0.05

TABLE 9

Effect of Sertoli cells on insulin content of incubated and frozen-thawed piglet islets.

| | Insulin content (uU/10 islet(s)) | |
|---|---|---|
| | Islets alone | Islets & Sertoli cells |
| Incubated D1 | 257 ± 19.6 | 391.1 ± 51.4* |
| Incubated D3 | 201.1 ± 19.1# | 400.1 ± 41.0*# |
| Incubated D7 | 179.1 ± 26.2# | 271.9 ± 39.9*# |
| Frozen D3/Thaw D3 | 52.4 ± 10.3 | 132.5 ± 35.1 |
| Frozen D7/Thaw D3 | 10.4 ± 0.9 | 35.1 ± 8.2 |

Anova *islets + Sertoli cells vs. islet alone P <0.05
Incubated islets D3, D7 vs. Frozen D3, D7 P <0.05

These results show that: (1) large numbers of neonatal porcine islets can be isolated by a simple method; (2) cryopreservation and thawing results in about 40% loss in number of islets in the absence of Sertoli cells and about a 20% loss in the presence of Sertoli cells; (3) cultured islets have the ability to respond to both glucose and glucose+Forskolin as insulin secretagogues; (4) the functional capacity of the co-cultured islet was enhanced two-fold in the presence of Sertoli cells; (5) following cryopreservation and thawing, islets recover more rapidly in presence of Sertoli cells and the response to both glucose and glucose+Forskolin was enhanced two fold in the presence of Sertoli cells.

I claim:

1. A method of treating a disease that results from a deficiency of a biological factor in a mammal wherein said method comprises administering Sertoli cells and a therapeutically effective amount of cells that produce said biological factor to a mammal in need of such treatment, wherein said Sertoli cells are administered in an amount effective to create an immunologically privileged site.

2. The method of claim 1 wherein said mammal is a human.

3. The method of claim 1 wherein said biological factor is a hormone.

4. The method of claim 1 wherein said biological factor is insulin and said disease is diabetes mellitus.

5. The method of claim 4 wherein said cells that produce said biological factor are pancreatic islet of Langerhans cells.

6. The method of claim 1 wherein said cells that produce said biological factor are cells transformed by a nucleic acid encoding said biological factor.

7. The method of claim 1 wherein said administering is by transplantation.

8. The method of claim 7 wherein said transplantation is by xenograft.

9. The method of claim 7 wherein said transplantation is by allograft.

10. The method of claim 1 wherein said Sertoli cells are administered in a dosage ranging from $10^5$ to $10^{10}$ cells.

11. The method of claim 1 wherein said cells that produce said biological factor are administered in a dosage of from $10^5$ to $10^{10}$ cells.

12. The method of claim 1 which further comprises administering an immunosuppressive agent.

13. The method of claim 12 wherein said immunosuppressive agent is administered for a time sufficient to permit said transplanted cells to be functional.

14. The method of claim 12 wherein said immunosuppressive agent is cyclosporine.

15. The method of claim 14 wherein said cyclosporine is administered at a dosage of from 5 to 40 mg/kg body wt.

16. The method of claim 1 which further comprises administering a therapeutically effective amount of exogenous biological factor following the transplantation of said cells that produce said biological factor.

17. The method of claim 1 wherein said cells that produce said biological factor are co-cultured with Sertoli cells in tissue culture.

18. The method of claim 17 wherein said cells that produce said biological factor are cryopreserved prior to co-culturing with Sertoli cells in tissue culture.

19. A method of treating diabetes mellitus in a mammal wherein said method comprises administering to a diabetic mammal Sertoli cells in an amount effective to create an immunologically privileged site and a therapeutically effective amount of pancreatic islet of Langerhans cells for release of insulin.

20. The method of claim 19 wherein said diabetes mellitus is type I or type II.

21. The method of claim 19 wherein said mammal is a human.

22. The method of claim 19 wherein said Sertoli cells are human, bovine or porcine.

23. The method of claim 19 wherein said pancreatic islet of Langerhans cells are human, bovine or porcine.

24. The method of claim 19 wherein said administering is by transplantation.

25. The method of claim 24 wherein said transplantation is by injection into the renal subcapsular space.

26. The method of claim 24 wherein said transplantation is by subcutaneous injection.

27. The method of claim 19 wherein said Sertoli cells are administered at a dosage ranging from $10^5$ to $10^{10}$ cells.

28. The method of claim 19 wherein said islet of Langerhans cells are administered at a dosage ranging from 5–1000 islet cells/g body wt.

29. The method of claim 19 which further comprises the administration of an effective amount of an immunosuppressive agent.

30. The method of claim 29 wherein said immunosuppressive agent is administered to maintain the release of insulin from the eyelet cells.

31. The method of claim 29 wherein said immunosuppressive agent is cyclosporine.

32. The method of claim 31 wherein said cyclosporine is administered at a dosage of 5 to 40 mg/kg body wt.

33. The method of claim 19 which further comprises administering a therapeutically effective amount of insulin following transplantation of said pancreatic islet of Langerhans cells.

34. A method of creating an immunologically privileged site in a mammal wherein said method comprises transplanting isolated Sertoli cells into a mammal.

35. The method of claim 34 wherein said mammal is a human.

36. The method of claim 34 wherein said Sertoli cells are injected into a renal subcapsular space.

37. The method of claim 34 wherein said Sertoli cells are subcutaneously injected into the mammal.

38. The method of claim 34 wherein said Sertoli cells are transplanted at a dosage ranging from $10^5$ to $10^{10}$ cells.

39. The method of claim 34 wherein said Sertoli cells are human, bovine or porcine.

40. A method of increasing the recovery and proliferation of biological factor producing cells ex vivo comprising co-culturing said cells with Sertoli cells under conditions sufficient to achieve said increased recovery and proliferation.

* * * * *

UNITED STATES PATENT AND TRADEMARK OFFICE
CERTIFICATE OF CORRECTION

PATENT NO. : 5,725,854
DATED : March 10, 1998
INVENTOR(S) : Helena P. Selawry

Page 1 of 2

It is certified that error appears in the above-identified patent and that said Letters Patent is hereby corrected as shown below:

On the Title page, item [54]: "AN" should read --AND--

Column 2, line 54: "122" should read --6:122--

Column 3, line 67: after "Oscar" insert --,--

Column 11, line 36: "197" should read --97--

Column 14, line 14: "127" should read --127†--

Column 14, line 15: "139 ,>418 ,>422 , >425 " should read --139†,>418†,>422†,>425† --

Column 14, line 16: ">287 ,305 ," should read -->287†,>305†,--

Column 14, line 17: ">306 ,>308 ,>441 ," should read -->306†,>308†,>441†, --

UNITED STATES PATENT AND TRADEMARK OFFICE
CERTIFICATE OF CORRECTION

PATENT NO. : 5,725,854
DATED : March 10, 1998
INVENTOR(S) : Helena P. Selawry

It is certified that error appears in the above-identified patent and that said Letters Patent is hereby corrected as shown below:

Column 18: ">447 ,>457 " should read -->447†,>457†--

Column 14, line 21: "challenged" should read --† challenged--

Signed and Sealed this

First Day of February, 2000

Attest:

Q. TODD DICKINSON

Attesting Officer

Acting Commissioner of Patents and Trademarks